United States Patent
Blobel et al.

(10) Patent No.: US 11,179,379 B2
(45) Date of Patent: Nov. 23, 2021

(54) COMPOSITIONS AND METHODS FOR HEMOGLOBIN PRODUCTION

(71) Applicants: THE CHILDREN'S HOSPITAL OF PHILADELPHIA, Philadelphia, PA (US); THE TRUSTEES OF THE UNIVERSITY OF PENNSYLVANIA, Philadelphia, PA (US); COLD SPRING HARBOR LABORATORY, Cold Spring Harbor, NY (US)

(72) Inventors: Gerd Blobel, Bala Cynwyd, PA (US); Jeremy Grevet, Philadelphia, PA (US); Junwei Shi, Philadelphia, PA (US); Christopher Vakoc, Cold Spring Harbor, NY (US)

(73) Assignees: THE CHILDREN'S HOSPITAL OF PHILADELPHIA, Philadelphia, PA (US); THE TRUSTEES OF THE UNIVERSITY OF PENNSYLVANIA, Philadelphia, PA (US); COLD SPRING HARBOR LABORATORY, Cold Spring Harbor, NY (US)

( * ) Notice: Subject to any disclaimer, the term of this patent is extended or adjusted under 35 U.S.C. 154(b) by 135 days.

(21) Appl. No.: 16/478,651

(22) PCT Filed: Jan. 30, 2018

(86) PCT No.: PCT/US2018/015918
§ 371 (c)(1),
(2) Date: Jul. 17, 2019

(87) PCT Pub. No.: WO2018/140934
PCT Pub. Date: Aug. 2, 2018

(65) Prior Publication Data
US 2019/0365734 A1    Dec. 5, 2019

Related U.S. Application Data

(60) Provisional application No. 62/452,069, filed on Jan. 30, 2017, provisional application No. 62/465,283, filed on Mar. 1, 2017.

(51) Int. Cl.
*A61K 31/454* (2006.01)
*A61P 7/06* (2006.01)
*A61K 31/517* (2006.01)
*C12N 15/113* (2010.01)
*A61K 45/06* (2006.01)

(52) U.S. Cl.
CPC .......... *A61K 31/454* (2013.01); *A61K 31/517* (2013.01); *A61P 7/06* (2018.01); *C12N 15/1137* (2013.01); *A61K 45/06* (2013.01)

(58) Field of Classification Search
None
See application file for complete search history.

(56) References Cited

U.S. PATENT DOCUMENTS

| 5,569,675 A | 10/1996 | Rephaeli et al. |
| 9,815,877 B2 | 11/2017 | Blobel et al. |
| 2003/0131363 A1 | 7/2003 | Chen |
| 2013/0123184 A1 | 5/2013 | Keegan et al. |
| 2014/0296320 A1 | 10/2014 | Dondero et al. |
| 2016/0045650 A1 | 2/2016 | Yoshida et al. |
| 2016/0096800 A1 | 4/2016 | Walter et al. |
| 2016/0130554 A1 | 5/2016 | Almeida-Porada et al. |
| 2016/0318856 A1 | 11/2016 | Aktas et al. |
| 2016/0318878 A1 | 11/2016 | Treon et al. |

FOREIGN PATENT DOCUMENTS

| WO | 2003/050252 A1 | 6/2003 | |
| WO | WO-2008128299 A1 * | 10/2008 | ................ A61P 7/06 |
| WO | 2012/162025 A1 | 11/2012 | |
| WO | 2016/118715 A1 | 7/2016 | |
| WO | 2016/135558 A2 | 9/2016 | |

OTHER PUBLICATIONS

Hahn, et al., "Eukaryotic initiation factor 2a phosphorylation mediates fetal hemoglobin induction through a post-transcriptional mechanism" Blood (2013) 122(4)1477-485.
Han, et al., "Heme-regulated eIF2α kinase (HRI) is required for translational regulation and survival of erythroid precursors in iron deficiency" Embo J. (2001) 20(23)16909-6918.
Chen, et al., "Translational Control by Heme-Regulated eIF2α Kinase during Erythropoiesis" Curr. Opin. Hematol. (2014)21(3):172-178.
Joshi, et al., "Small molecule modulators of eukaryotic initiation factor 2a kinases, the key regulators of protein synthesis" Biochimie (2013) 95:1980-1990.
Kanelakis, et al., "Functional Characterization of the Canine Heme-Regulated eIF2α Kinase: Regulation of Protein Synthesis" Advances in Hematology (2009) 2009:251915.
Miksanova, et al., "Characterization of Heme-Regulated eIF2R Kinase: Roles of the N-Terminal Domain in the Oligomeric State, Heme Binding, Catalysis, and Inhibition" Biochemistry (2006) 45:9894-9905.
Rosenm, et al., "Discovery of the first known small-molecule inhibitors of heme-regulated eukaryotic initiation factor 2a (HRI) kinase" Bioorganic & Medicinal Chemistry Letters (2009) 19:6548-6551.

* cited by examiner

*Primary Examiner* — Tracy Vivlemore
(74) *Attorney, Agent, or Firm* — Robert C. Netter, Jr.; Dann, Dorfman, Herrell & Skillman

(57) ABSTRACT

Methods and compositions for producing fetal hemoglobin and treating a hemoglobinopathy or thalassemia are disclosed.

Figure 1A:
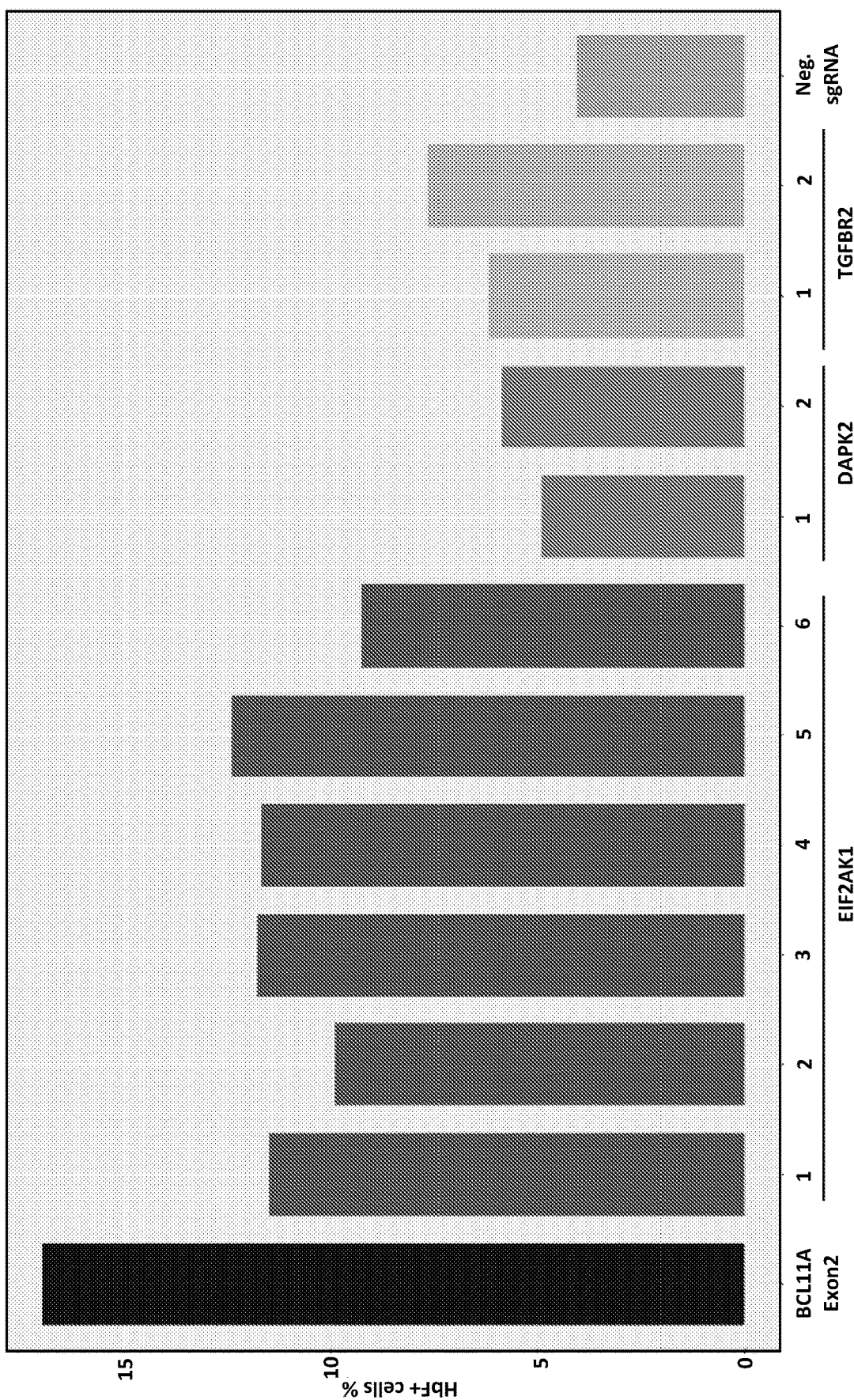

16 Claims, 15 Drawing Sheets
Specification includes a Sequence Listing.

```
  1 MQGGNSGVRK REEEGDGAGA VAAPPAIDFP AEGPDPEYDE SDVPAEIQVL KEPLQQPTFP
 61 FAVANQLLLV SLLEHLSHVH EPNPLRSRQV FKLLCQTFIK MGLLSSFTCS DEFSSLRLHH
121 NRAITHLMRS AKERVRQDPC EDISRIQKIR SREVALEAQT SRYLNEFEEL AILGKGGYGR
181 VYKVRNKLDG QYYAIKKILI KGATKTVCMK VLREVKVLAG LQHPNIVGYH TAWIEHVHVI
241 QPRADRAAIE LPSLEVLSDQ EEDREQCGVK NDESSSSSII FAEPTPEKEK RFGESDTENQ
301 NNKSVKYTTN LVIRESGELE STLELQENGL AGLSASSIVE QQLPLRRNSH LEESFTSTEE
361 SSEENVNFLG QTEAQYHLML HIQMQLCELS LWDWIVERNK RGREYVDESA CPYVMANVAT
421 KIFQELVEGV FYIHNMGIVH RDLKPRNIFL HGPDQQVKIG DFGLACTDIL QKNTDWTNRN
481 GKRTPTHTSR VGTCLYASPE QLEGSEYDAK SDMYSLGVVL LELFQPFGTE MERAEVLTGL
541 RTGQLPESLR KRCPVQAKYI QHLTRRNSSQ RPSAIQLLQS ELFQNSGNVN LTLQMKIIEQ
601 EKEIAELKKQ LNLLSQDKGV RDDGKDGGVG
```

Figure 7A

```
   1 ccccagtgaa ggtgcgcgcg tggcggaggc tggttttccg tctggtgagg ggttacttcc
  61 gggtcggacg gcgctagctg cagcatcgga gtgtggcagt gctgggctgg ccggcgggct
 121 gggctgcggc ccgcgcgcgg ccggcatgc aggggggcaa ctccggggtc cgcaagcgcg
 181 aagaggaggg cgacggggct ggggctgtgg ctgcgccgcc ggccatcgac tttcccgccg
 241 agggcccgga ccccgaatat gacgaatctg atgttccagc agaaatccag gtgttaaaag
 301 aaccccctaca acagccaacc ttcccttttg cagttgcaaa ccaactcttg ctggtttctt
 361 tgctggagca cttgagccac gtgcatgaac caaacccact tcgttcaaga caggtgttta
 421 agctactttg ccagacgttt atcaaaatgg ggctgctgtc ttcttttcact tgtagtgacg
 481 agtttagctc attgagacta catcacaaca gagctattac tcacttaatg aggtctgcta
 541 aagagagagt tcgtcaggat ccttgtgagg atatttctcg tatccagaaa atcagatcaa
 601 gggaagtagc cttggaagca caaacttcac gttacttaaa tgaatttgaa gaacttgcca
 661 tcttaggaaa aggtggatac ggaagagtat acaaggtcag gaataaatta gatggtcagt
 721 attatgcaat aaaaaaaatc ctgattaagg gtgcaactaa aacagtttgc atgaaggtcc
 781 tacgggaagt gaaggtgctg gcaggtcttc agcacccccaa tattgttggc tatcacaccg
 841 cgtggataga acatgttcat gtgattcagc cacgagcaga cagagctgcc attgagttgc
 901 catctctgga agtgctctcc gaccaggaag aggacagaga gcaatgtggt gttaaaaatg
 961 atgaaagtag cagctcatcc attatctttg ctgagcccac cccagaaaaa gaaaaacgct
1021 ttggagaatc tgacactgaa aatcagaata caagtcggt gaagtacacc accaatttag
1081 tcataagaga atctggtgaa cttgagtcga ccctggagct ccaggaaaat ggcttggctg
1141 gtttgtctgc cagttcaatt gtggaacagc agctgccact caggcgtaat cccacctag
1201 aggagagttt cacatccacc gaagaatctt ccgaagaaaa tgtcaacttt ttgggtcaga
1261 cagaggcaca gtaccacctg atgctgcaca tccagatgca gctgtgtgag ctctcgctgt
1321 gggattggat agtcgagaga aacaagcggg gccgggagta tgtggacgag tctgcctgtc
1381 cttatgttat ggccaatgtt gcaacaaaaa ttttcaaga attggtagaa ggtgtgtttt
1441 acatacataa catgggaatt gtgcaccgag atctgaagcc aagaaatatt tttcttcatg
1501 gccctgatca gcaagtaaaa ataggagact ttggtctggc ctgcacagac atcctacaga
1561 agaacacaga ctggaccaac agaaacggga agaacacc aacacatacg tccagagtgg
1621 gtacttgtct gtacgcttca cccgaacagt tggaaggatc tgagtatgat gccaagtcag
1681 atatgtacag cttgggtgtg gtcctgctag agctctttca gccgtttgga acagaaatgg
1741 agcgagcaga agttctaaca ggtttaagaa ctggtcagtt gccggaatcc ctccgtaaaa
1801 ggtgtccagt gcaagccaag tatatccagc acttaacgag aaggaactca tcgcagagac
1861 catctgccat tcagctgctg cagagtgaac ttttccaaaa ttctggaaat gttaacctca
1921 ccctacagat gaagataata gagcaagaaa aagaaattgc agaactaaag aagcagctaa
1981 acctcctttc tcaagacaaa ggggtgaggg atgacggaaa ggatggggc gtgggatgaa
2041 agtggactta acttttaagg tagttaactg gaatgtaaat ttttaatctt tattagggta
2101 tagttggtac aatgcttcgt tgtatttagt aagcctttac aagacttgtt aaagatgtca
2161 gagtgcccca agctgccgtt ccttcccttc ctgccccaca agctcctttt cctgaatttc
2221 ctacctaaat attaaccata tgcctagtct ctgaaactaa aaacttggac ctcatcctca
2281 attattttct cctttcaact ctgttgaccc tctgtctggt cttcctctag aaggtaccgc
2341 agaaattgat gtgtgctccc tgccctcgtc actgcccaag cccgggcctg cacatactca
2401 ctggactgtt ccagttttga cagctgccag tcttcctgcc cctttcacac tgcagctgaa
2461 gttcattacc tgaaggacgc ctcatcattt cattccttgg ctccaaacct tctgctgcct
2521 ctaagataaa agctcaactt cttaacagtg tacagtgtgc aacttccaac ctttttatct
2581 gttctctcca ccttcagttt agcgtcattc caaaaccaca cccttgcaaa gctttgtact
2641 ccgcacccca gatgatctcc aggcagctca gatctctttc ctgcctttgc cctgcactgt
2701 tccccggtac ttcctccttt attgtagcac tcagctcccc agccaatctg tacatccctc
2761 agaggcagcg atctgatgaa ttggtttttg aatcccagaa agggtctgcc atggagttgg
2821 cagtcatcac ggtagatggc gtatgatttt gctgaatttt aaataaaatg aaaaccataa
2881 attacatgat gcttttattg acacttgaca actggcctaa ataaaagac tctgactcta
2941 atacaagtcc ccttactgat aataggcatg aaagagcacc attcttaaaa tctaaaccct
3001 ttaaaatcag ttacggcaat tcacttaagg agcttgaggg ccgtgttaaa aggagccagg
3061 ttttcacaag acctcatcca cctctgcaca ttggctggca ctgtcacact gcagcctccg
3121 atctgctgga gtacagacca cagcaccacg tctgctacgg tgagttcatt cccagcgagc
3181 caagggctct tcccaagagc agagttcatg gagcggaaaa cagcggcttt ttctttactg
3241 cttccctctt ttaactgaaa aatcgcaata tctacccagc tatctataag ggttgcgttg
```

Figure 7B

```
3301 acagcattat gcttctggcc aaacagagag aacaagaaac gtgcaatgtt cccttcgcct
3361 tcgatggggc acatcgtctg gatgctgaat ttcatctgcg tcttcggcac tgaaaagaaa
3421 aaacacgcca ggtagcatca ccagagcagc cctgagggaa gtactcgcac agtggggaag
3481 gggacagtca ccaaacacca cagactgatg acatgggaaa gggtgttttc aagaagaaca
3541 tcacattttc agtctgtctc taagatgctt actactgaaa agggtttaag tgcaaactat
3601 gttaaaaaag taaccaaaga gtcattcctg gtatttgatt atgacacttc tgaagctaga
3661 agggacctca gaccacctgc tccaatccct gctgcctaag gttttggggg ctgagggctg
3721 gaaacccagg agctgcatct cccaggctct tggcctcata atcgccttct gtgagactga
3781 gggcaattaa gatatgaatg acatgaactc gcttatctcc atatcaacat aaaccagaag
3841 aggcatacat ctgtgggata gtcaatacat aacatcctat ctttatatgg ccatatgaga
3901 agataacttc agtgtcccta tgatggtaag ttcttgaatg tgagggcaag atggctgtga
3961 tagccatgac tccccgcttt gcctggttgg acagaacccc cttccccaaa tgctcacagt
4021 ccccccttg agctgtgtct cactcagaga ccctaaattt tgcagacgaa caagggcatc
4081 tttgcgttgc ttcatctctg ctcctcctct agaactatcc cacaggcttt ctagacttag
4141 aatatctgac ctgatgcaaa tcgctatgtg gccagtatgc cacagaatgt cctaaaccct
4201 tgctgcctct tatcaaaacc atgttgcaca tctcatcata tagtacagct aaccettgaa
4261 cagtgggggg gttaggaca ctgaccccg actgctgtgc agtcgaaaat ccacataaaa
4321 cttctgactc cttcaaaact taagcactaa tagcctacta ttcatgggaa gccttaccca
4381 tcacagttga ttaacacgtt ttgtatggtc tgtatattat atgctatatt cttacaataa
4441 acttgagaaa atgttaagaa aataa
```

Figure 7C

COMPOSITIONS AND METHODS FOR HEMOGLOBIN PRODUCTION

This application is a § 371 application of PCT/US2018/015918, filed Jan. 30, 2018, which claims priority under 35 U.S.C. § 119(e) to U.S. Provisional Patent Application No. 62/452,069, filed Jan. 30, 2017 and U.S. Provisional Patent Application No. 62/465,283, filed Mar. 1, 2017. The foregoing applications are incorporated by reference herein.

This invention was made with government support under Grant Nos. R37DK058044, R01DK054937, and R01HL119479 awarded by National Institutes of Health. The government has certain rights in the invention.

FIELD OF THE INVENTION

The present invention relates to the field of hematology. More specifically, the invention provides compositions and methods for the production of various forms of hemoglobin, including adult and fetal type hemoglobin.

BACKGROUND OF THE INVENTION

Several publications and patent documents are cited throughout the specification in order to describe the state of the art to which this invention pertains. Each of these citations is incorporated herein by reference as though set forth in full.

Sickle cell disease and thalassemia cause significant worldwide morbidity and mortality (Modell et al. (2008) Bull. World Health Org., 86:480-487). However, effective drugs do not exist for these illnesses. One goal in the treatment of these diseases is to reactivate fetal hemoglobin (HbF). HbF reduces the propensity of sickle cell disease red blood cells to undergo sickling. Indeed, high fetal globin levels are associated with improved outcomes for sickle cell anemia patients (Platt et al. (1994) N. Engl. J. Med., 330:1639-1644). Elevating HbF also reduces the globin chain imbalance in certain thalassemias, thereby improving symptoms. There is an enormous unmet need to identify compounds that ameliorate the course of these diseases.

SUMMARY OF THE INVENTION

In accordance with the present invention, compositions and methods are provided for increasing hemoglobin levels (e.g., fetal hemoglobin) in a cell or subject. In a particular embodiment, the method comprises administering at least one eIF2αK1 inhibitor to the cell or subject. In a particular embodiment, the subject has a hemoglobinopathy such as sickle cell disease or thalassemia. In a particular embodiment, the cell is an erythroid cell. In a particular embodiment, the eIF2αK1 inhibitor is a small molecule. The eIF2αK1 inhibitor may be, for example, a kinase domain inhibitor or a heme binding domain inhibitor. The eIF2αK1 inhibitor may be a CRISPR based or siRNA/shRNA based inhibitor of the eIF2αK1 gene. The method may further comprise delivering at least one fetal hemoglobin inducer to the cell or subject. The method may further comprise the administration of other fetal hemoglobin inducing methods (e.g., pharmacologic compounds or various forms of gene therapy) in order to produce additive or synergistic effects.

In accordance with another aspect of the instant invention, methods of inhibiting, treating, and/or preventing a hemoglobinopathy (e.g., sickle cell disease or thalassemia) in a subject are provided. In a particular embodiment, the method comprises administering at least one eIF2αK1 inhibitor to a subject in need thereof. The eIF2αK1 inhibitor may be in a composition with a pharmaceutically acceptable carrier. In a particular embodiment, the subject has a β-chain hemoglobinopathy. In a particular embodiment, the subject has sickle cell anemia. In a particular embodiment, the eIF2αK1 inhibitor is a small molecule. The eIF2αK1 inhibitor may be, for example, a kinase domain inhibitor or a heme binding domain inhibitor. The eIF2αK1 inhibitor may be a CRISPR based or siRNA/shRNA based inhibitor of the eIF2αK1 gene. The method may further comprise delivering at least one other fetal hemoglobin inducer to the subject.

BRIEF DESCRIPTIONS OF THE DRAWINGS

Figure 1B:
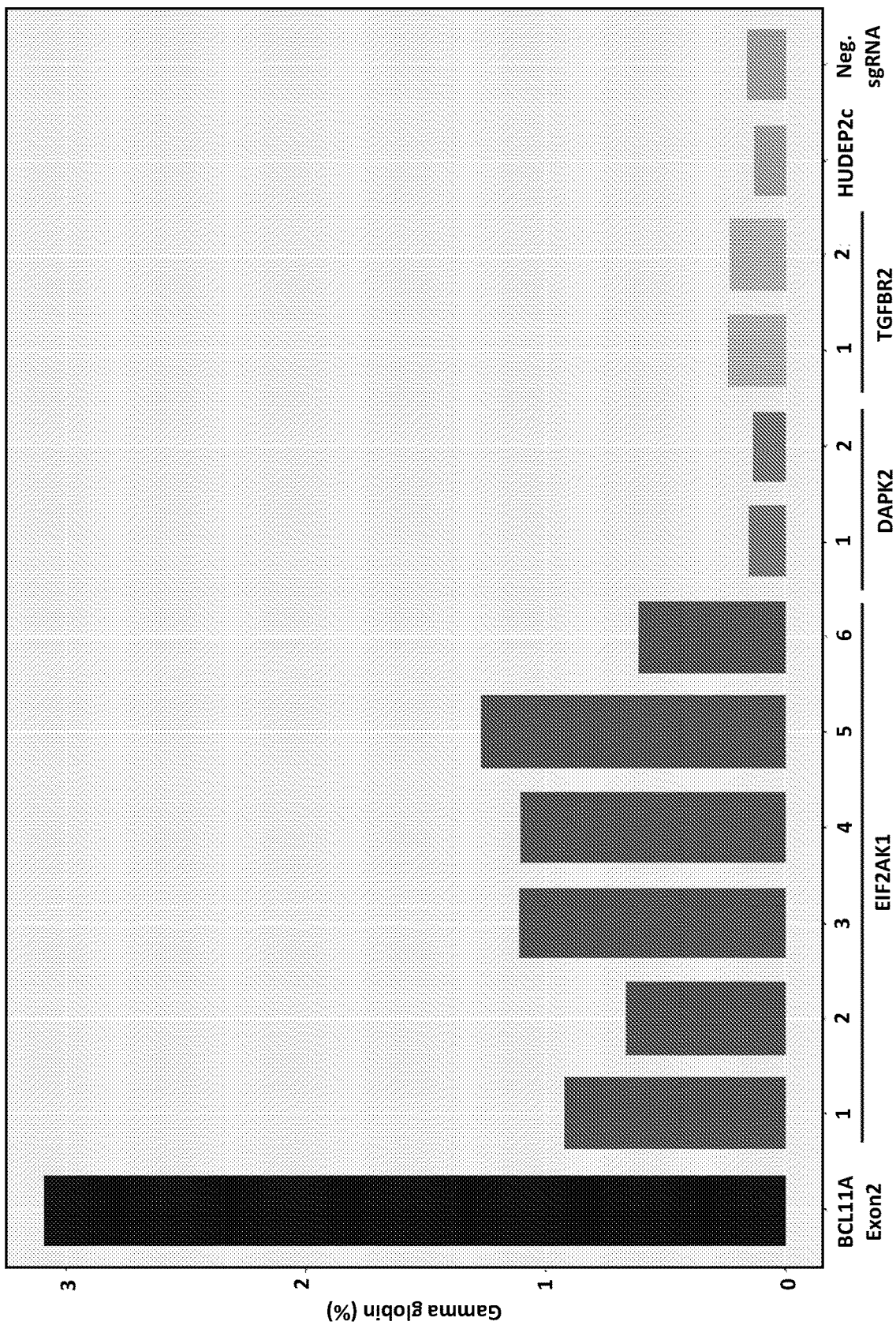
Figure 1C:
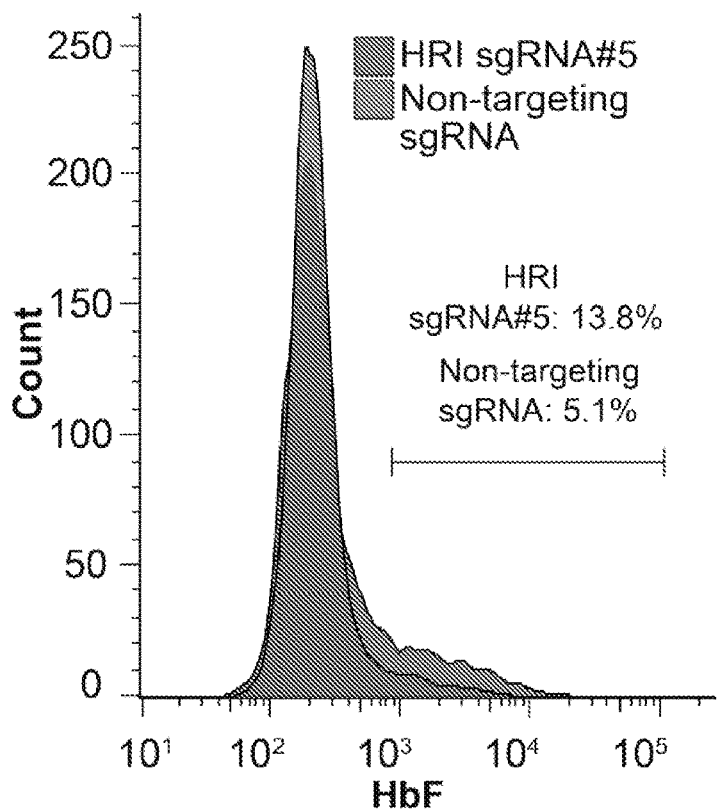
Figure 1D:
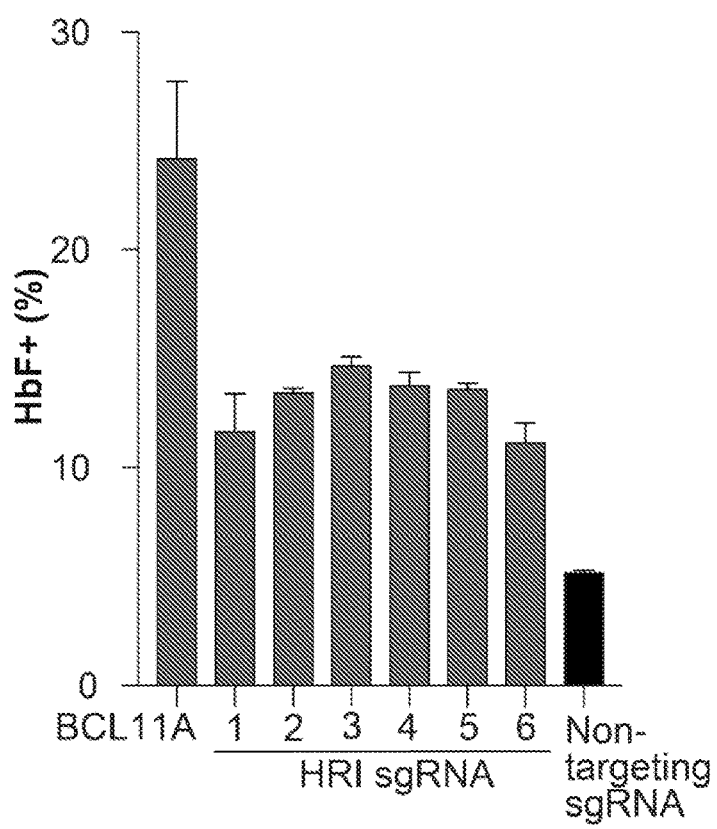
Figure 1E:
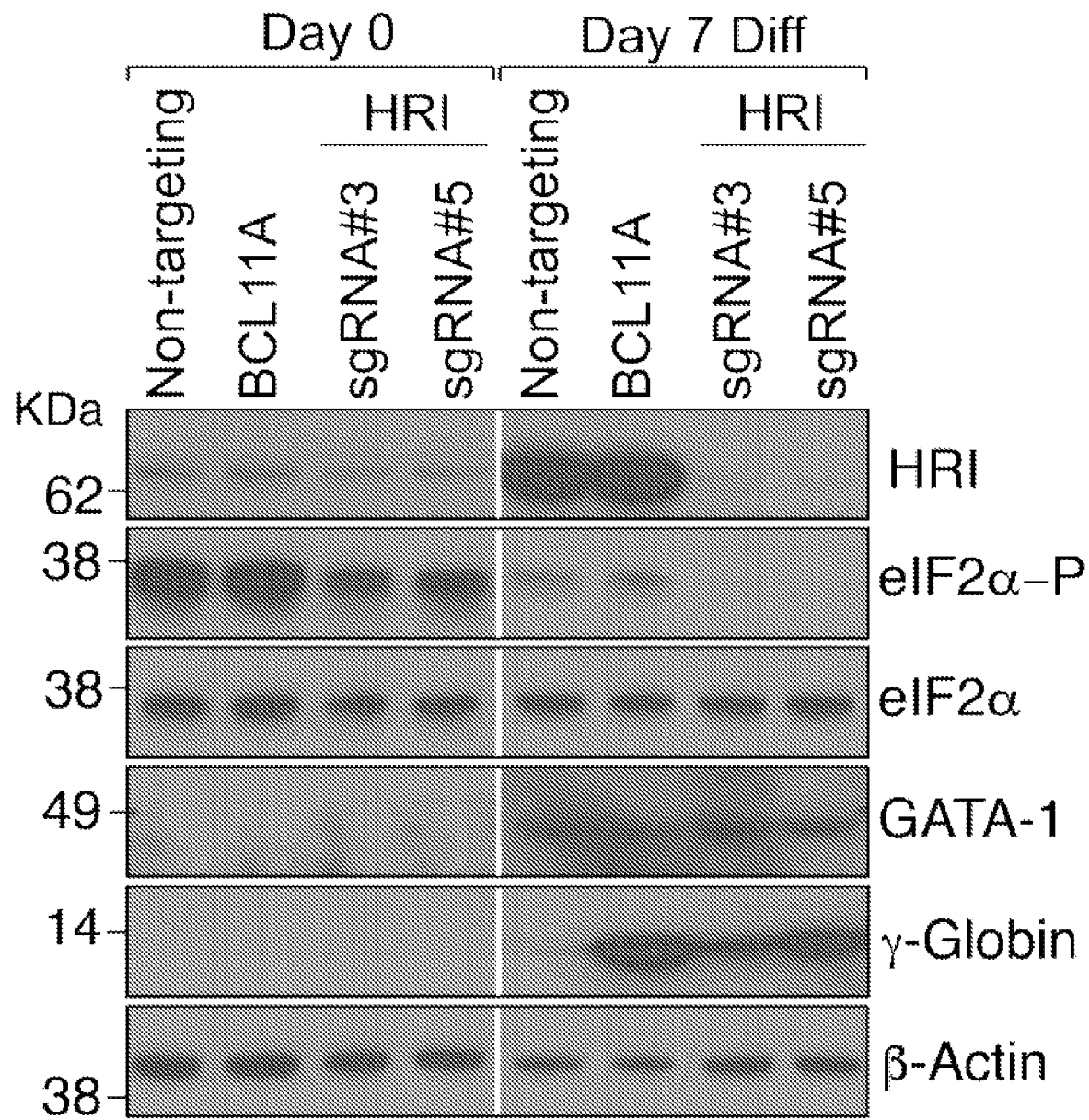

FIG. 1A is a graph of the percentage of cells that are positive for fetal hemoglobin (HbF) expression. Human umbilical cord blood-derived erythroid progenitor cells (HUDEP-2) expressing Cas9 were transduced with one of the six guideRNAs targeting eIF2αK1; a guideRNA targeting BCL11A exon 2 (positive control; BCL11A is a repressor of HbF expression); one of two guideRNAs targeting death associated protein kinase 2 (DAPK2); one of two guideRNAs targeting transforming growth factor beta receptor 2 (TGFBR2); or a negative control guideRNA. FIG. 1B is a graph of the gamma globin mRNA levels in the cells of FIG. 1A. A negative control of untreated cells is also provided. FIG. 1C is a representative HbF FACS analysis for HUDEP-2 cells expressing sgRNA #5 or non-targeting sgRNA. FIG. 1D is a graph of the percentage of HUDEP-2 cells that are positive for HbF expression. Mean is shown±standard deviation from biological replicates (n=2). FIG. 1E is a Western blot analysis of various proteins in HUDEP-2 cells transduced with BCL11A exon 2 sgRNA, sgRNA #3, sgRNA #5, or non-targeting sgRNA.

Figure 2:
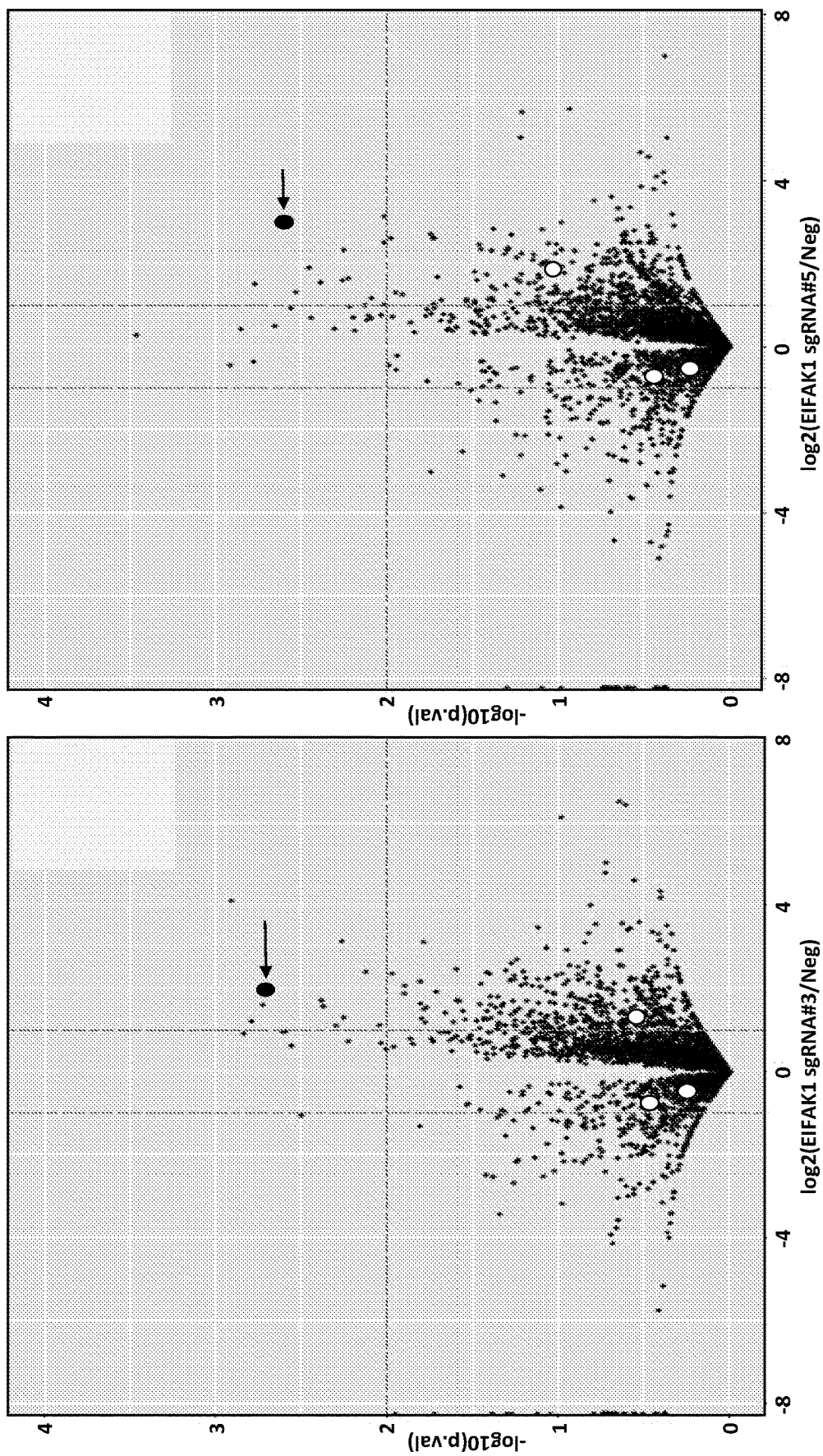

FIG. 2 provides the results of a whole proteome mass spectrometry analysis of cells transduced with a guideRNA targeting eIF2αK1 compared to a negative control guideRNA. Left panel is for cells transduced with eIF2αK1 sgRNA #3 and right panel is for cells transduced with eIF2αK1 sgRNA #5. Black ovals with arrow indicate fetal globin expression. White ovals—zeta globin; ovals with vertical lines—adult β-globin; ovals with horizontal lines—adult α-globin. Vertical dashed lines indicate a 2 fold change. Horizontal dashed line indicates a p-value of 0.01.

Figure 3:
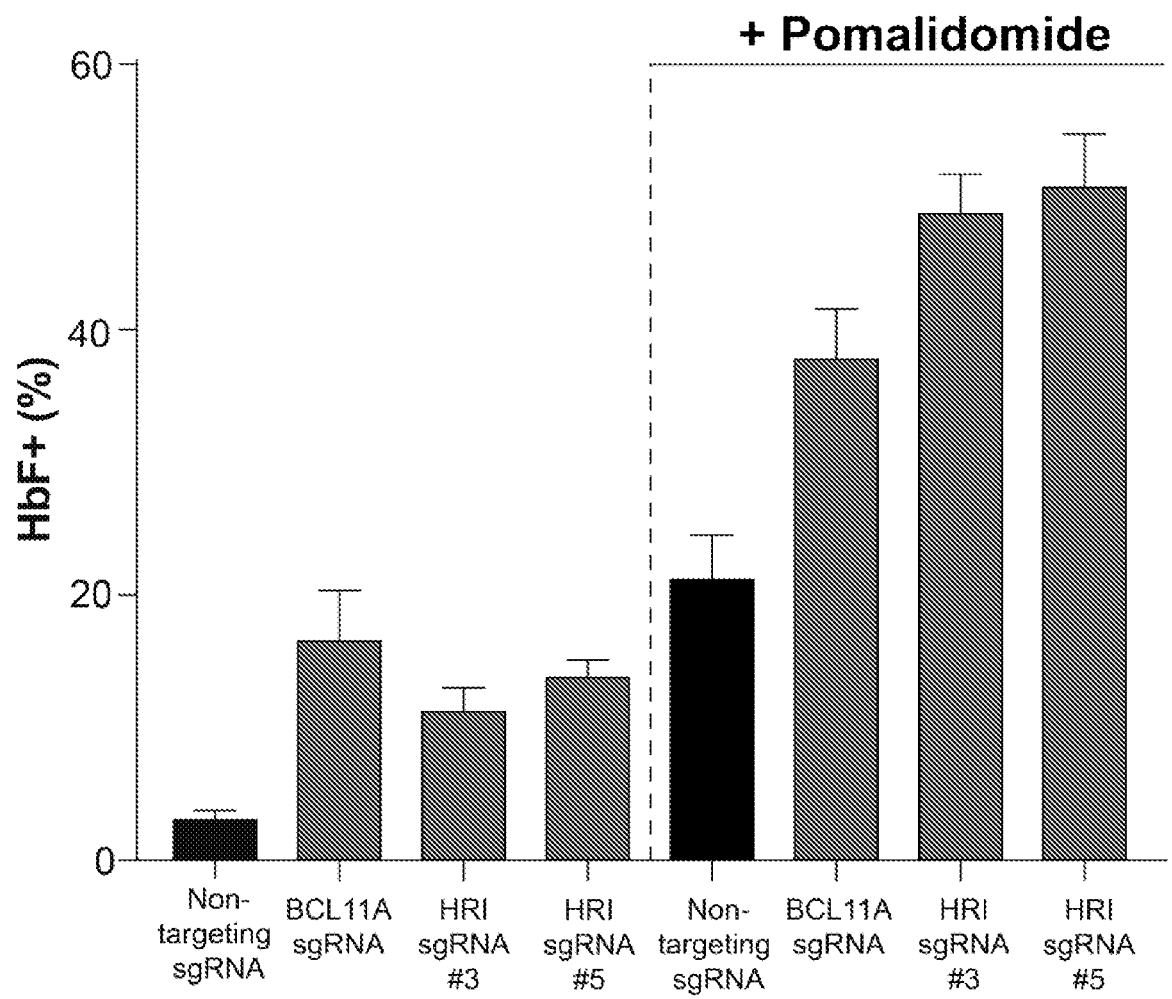

FIG. 3 is a graph of the percentage of cells positive for HbF expression. HUDEP-2 expressing Cas9 cells were transduced with eIF2αK1 sgRNA #3, eIF2αK1 sgRNA #5, a gRNA targeting BCL11A exon 2, or a negative control gRNA. Cells were then incubated with or without pomalidomide. n=3.

Figure 4:
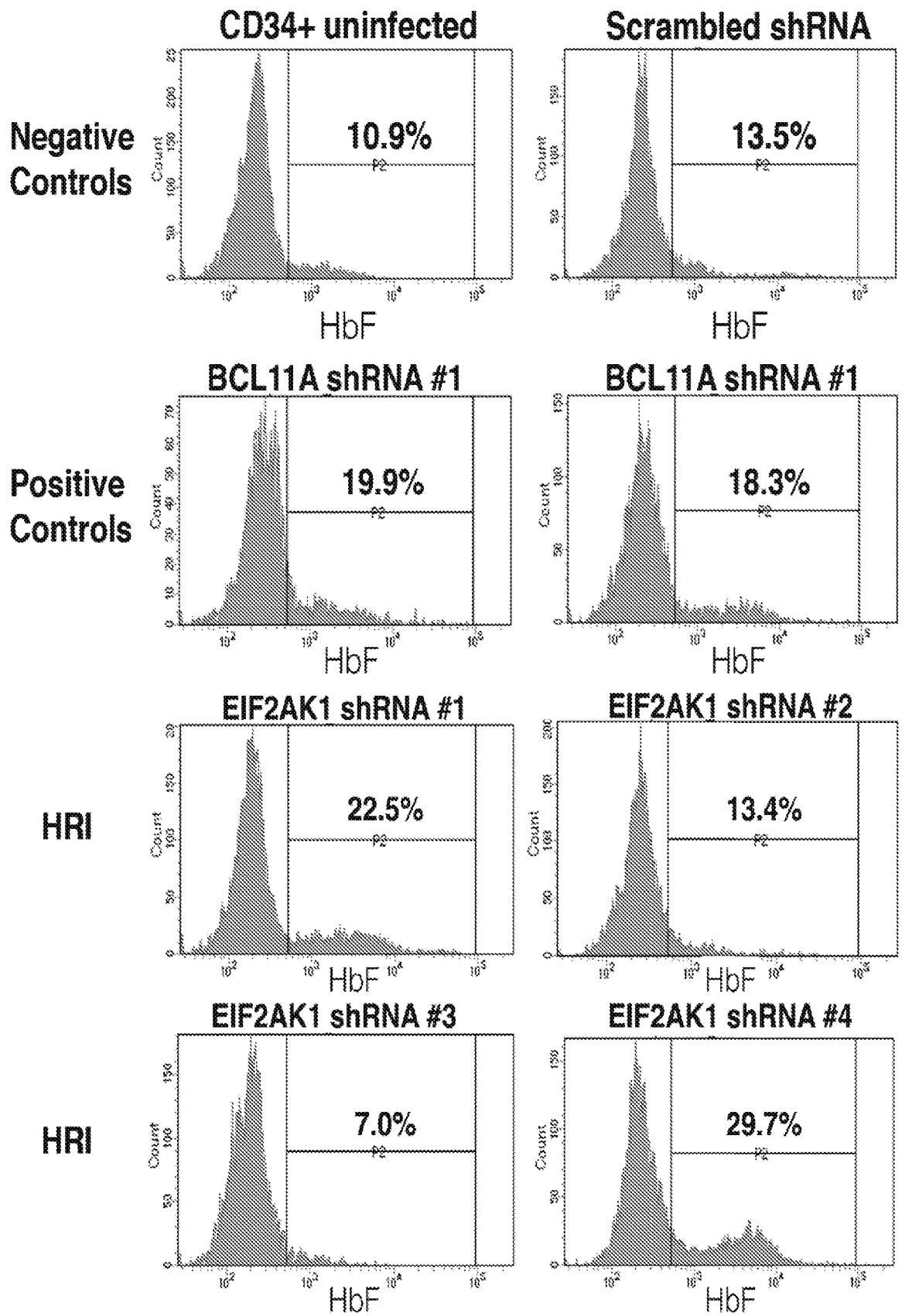

FIG. 4 provides graphs of the expression of HbF in human primary cells treated with eIF2αK1 shRNA, BCL11A shRNA, or scrambled shRNA (negative control).

Figure 5A:
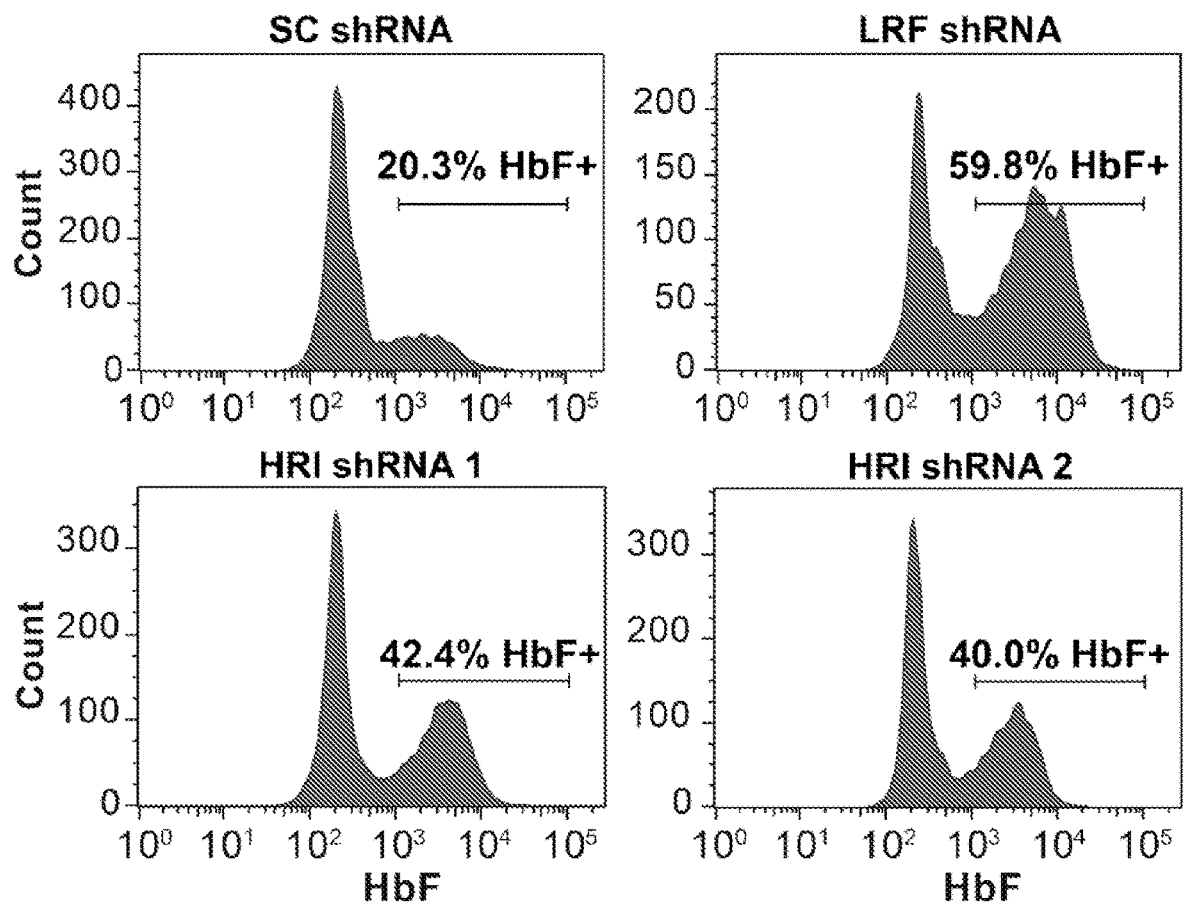
Figure 5B:
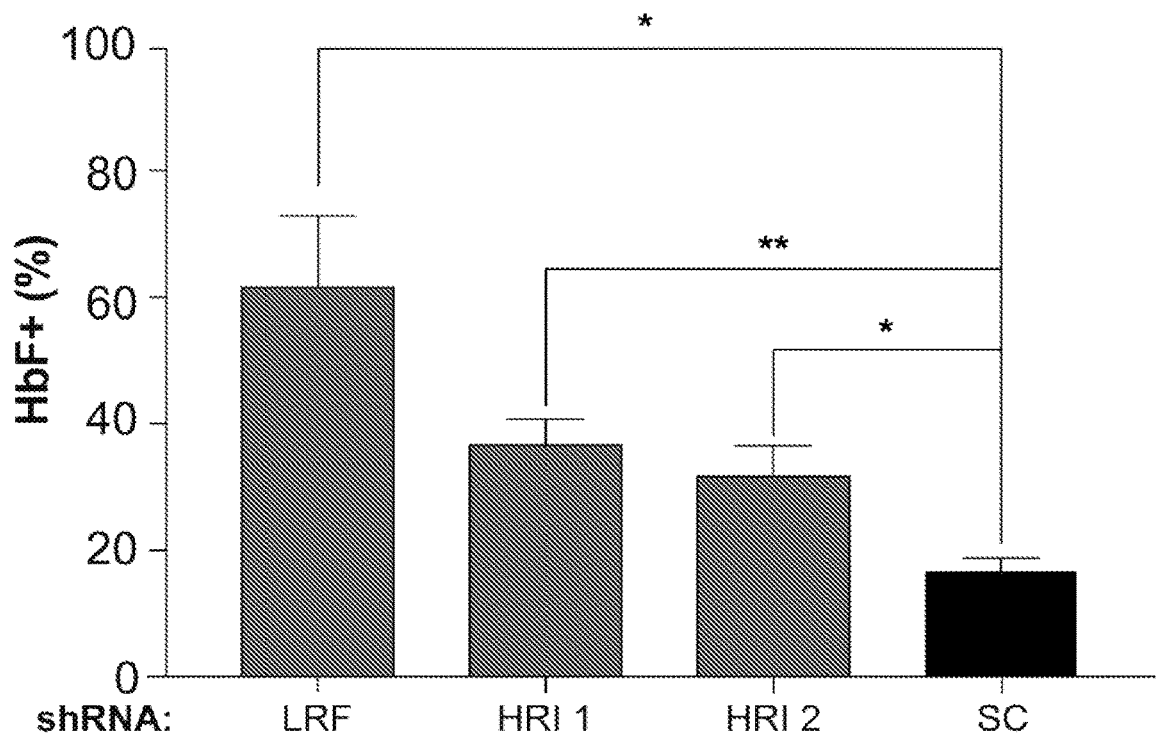
Figure 5C:
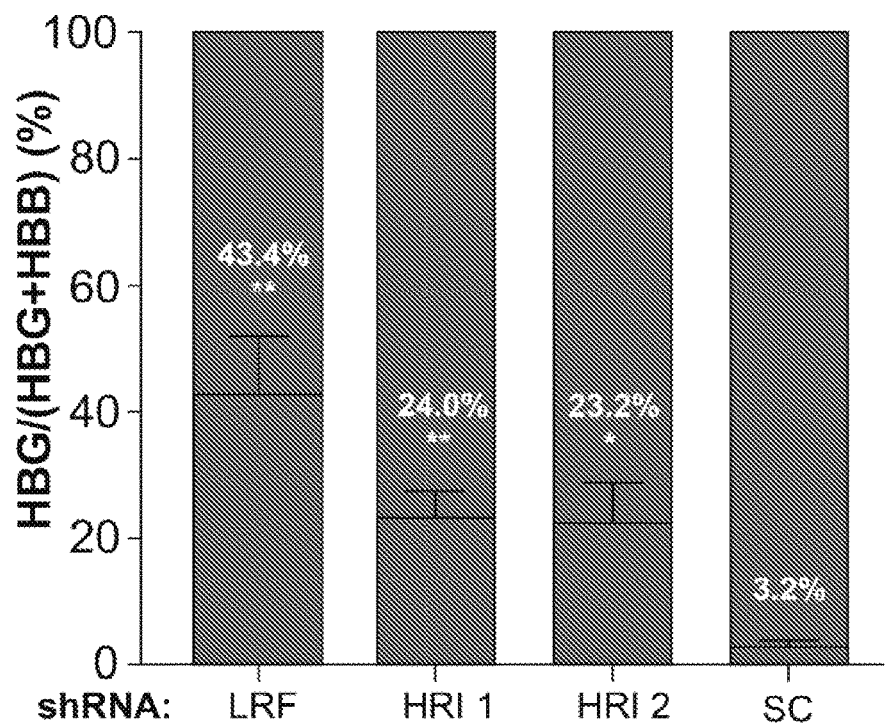
Figure 5D:
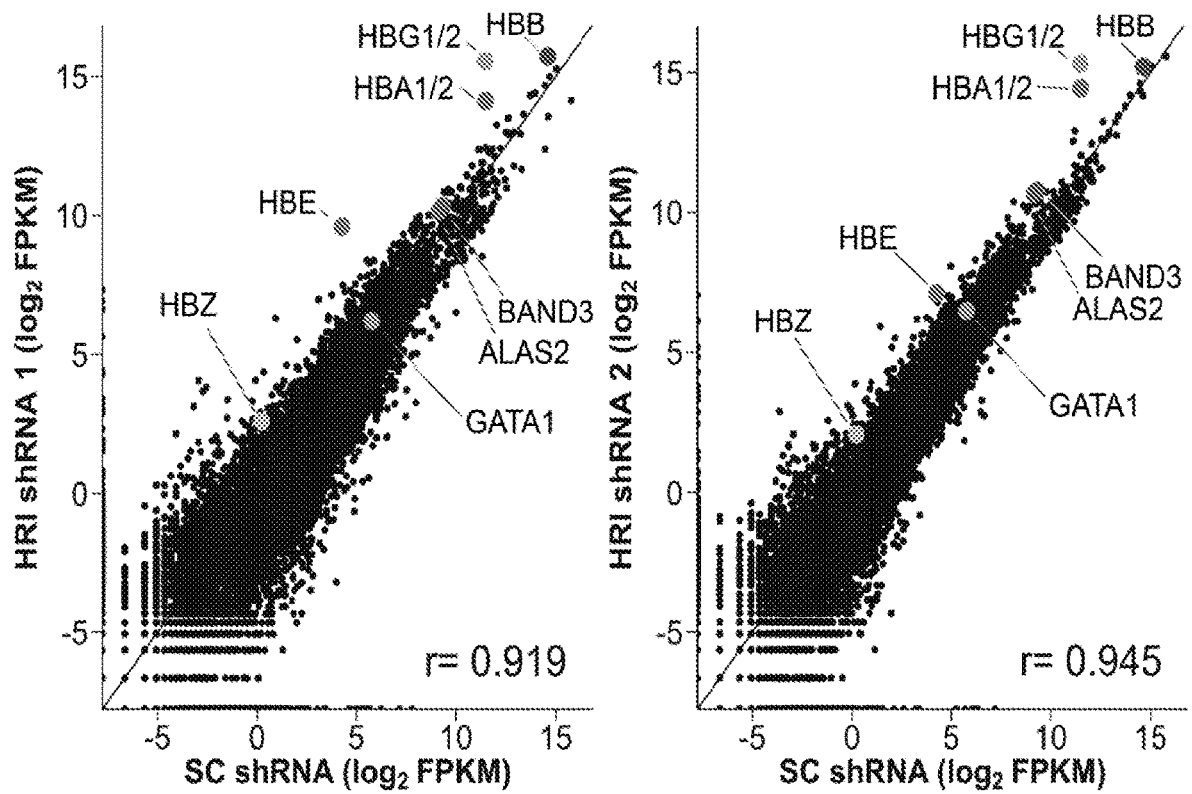
Figure 5E:
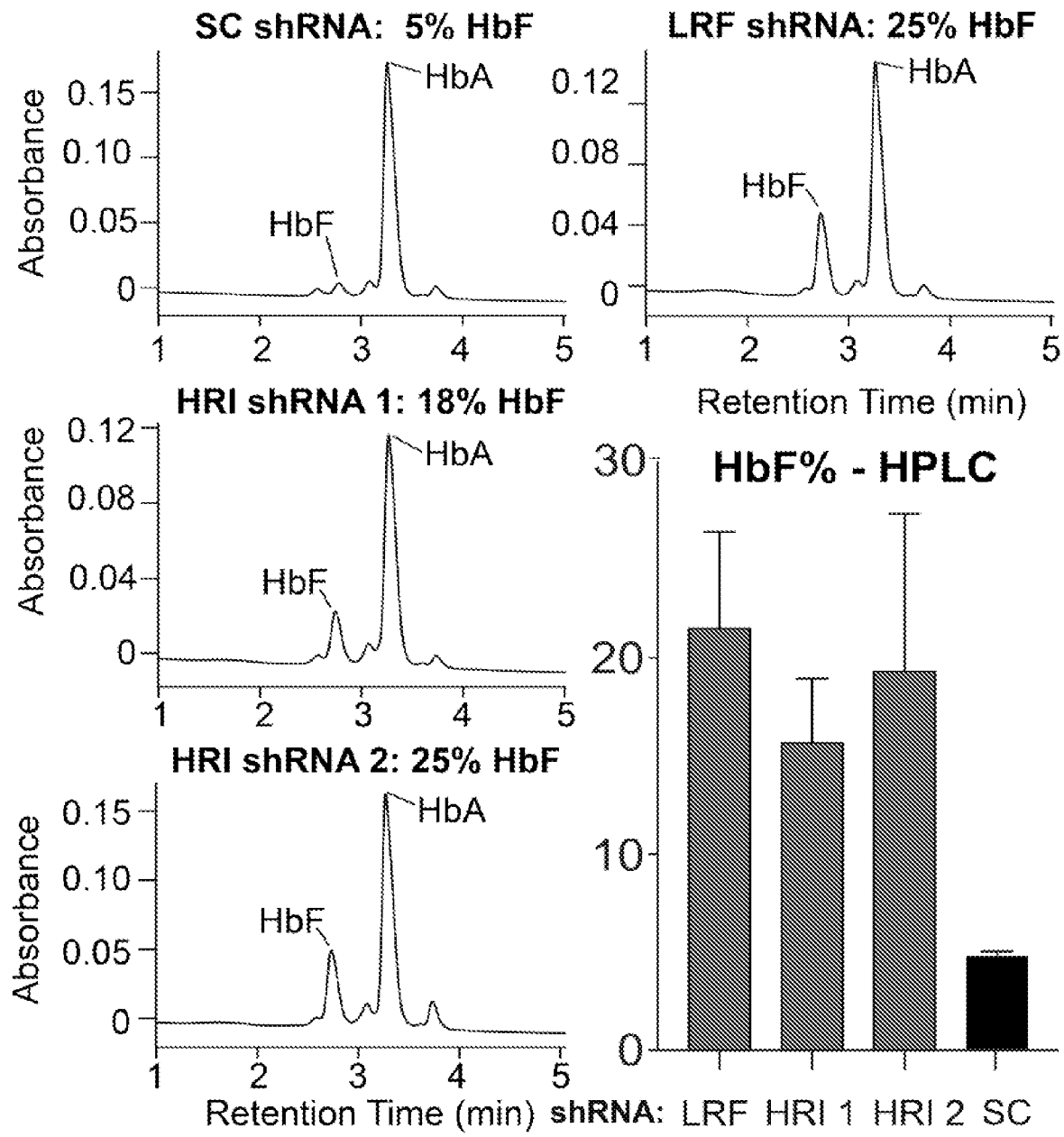
Figure 5F:
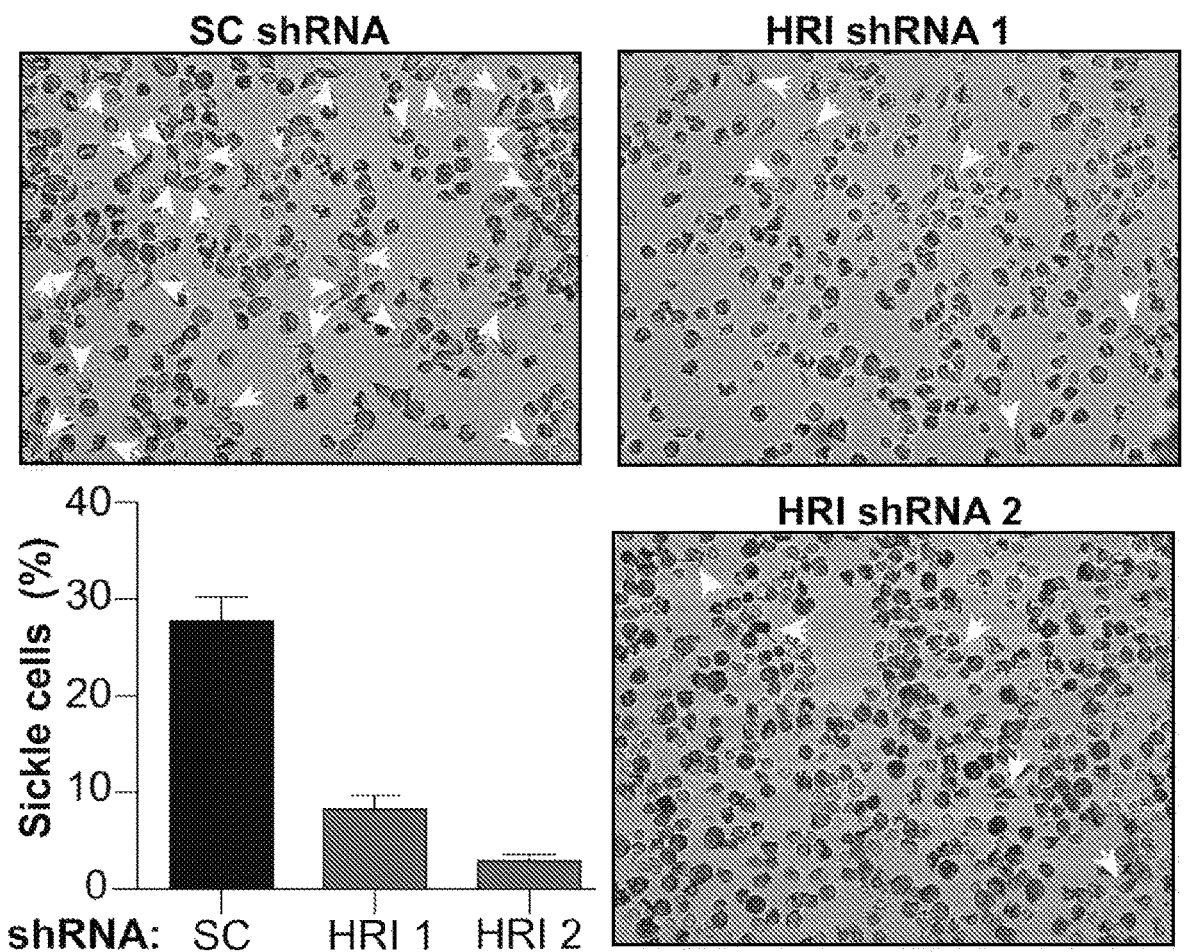

FIG. 5A provides representative HbF flow cytometry on day 14 of CD34+ erythroid differentiation. FIG. 5B provides a graph of HbF flow cytometry experiments. Error bars: SEM from 3 independent donors (* denotes p-value<0.05, ** denotes p-value<0.01 from unpaired student T-tests). FIG. 5C shows γ-globin mRNA as fraction of γ-globin+β-globin by RT-qPCR on day 12. Error bars: SEM from 3 independent donors (* denotes p-value<0.05, ** denotes p-value<0.01 from unpaired student T-tests). FIG. 5D shows the RNA-seq for CD34+ cells on day 12. R-value denotes Pearson correlation coefficient. Data was obtained from one patient donor. FIG. 5E shows HPLC analysis of samples from cell expressing annotated shRNAs, at day 14 of differentiation. HbA: hemoglobin A (adult form). HbF: fetal hemoglobin. Error bars: standard deviation from 2 independent donors. FIG. 5F provides images of sickle cell patient-derived erythroid cultures. Arrow heads mark cells with sickle-like morphology. Bar graph: summary of blindly counted sickle shaped cells from 3 fields from one patient with sickle cell disease.

Figure 6A:
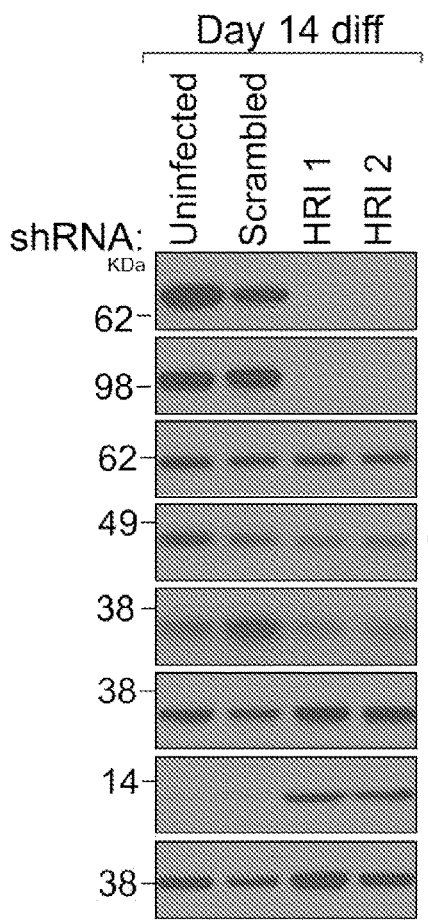
Figure 6A:
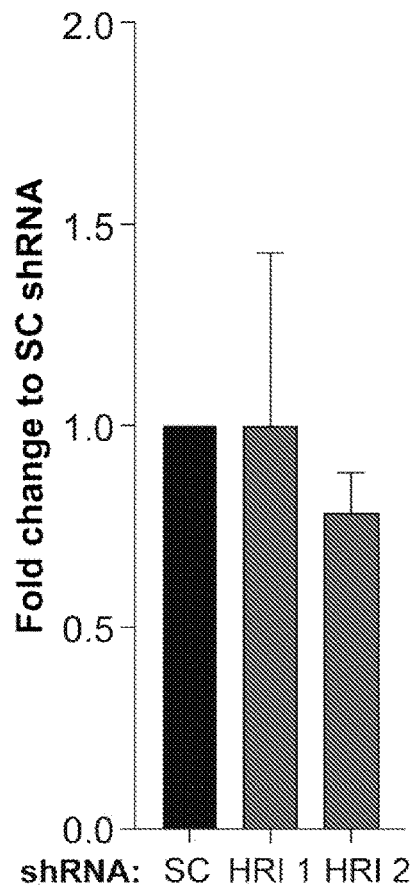
Figure 6B:
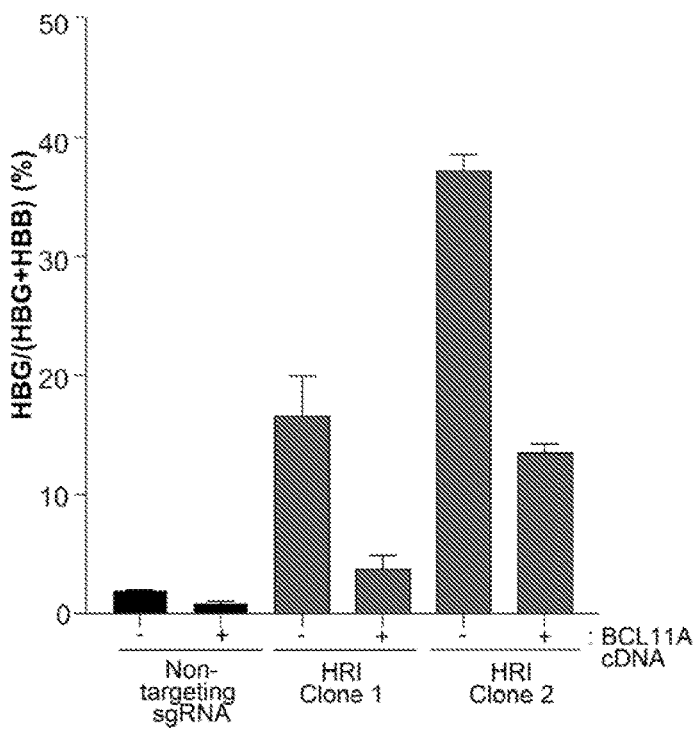

FIG. 6A provides a Western blot with indicated antibodies in cells uninfected, or infected with virus expressing scrambled or HRI shRNAs on day 14 of differentiation (left). BCL11A mRNA levels in HRI knock down cells as fraction of SC shRNA expressing cells is also shown (right). Error bars standard deviation from two biological replicates. FIG. 6B shows RT-qPCR for γ-globin as a fraction of γ-globin+β-globin in a BCL11A cDNA rescue in HRI depleted HUDEP2 clonal cell line. Error bars: standard deviation from two biological replicates.

FIG. 7A provides an example of an amino acid sequence (SEQ ID NO: 19) of eIF2αK1 and FIGS. 7B and 7C provide an example of a nucleotide sequence (SEQ ID NO: 20) encoding eIF2αK1.

DETAILED DESCRIPTION OF THE INVENTION

A major goal in the treatment of sickle cell disease and thalassemia is the reactivation of fetal type globin expression in cells of the adult red blood lineage. In an unbiased genetic screen, the protein kinase eIF2αK1 (eukaryotic translation initiation factor 2-alpha kinase 1; also known as Heme-Regulated Inhibitor (HRI)) was identified as a strong regulator of fetal globin production. eIF2αK1 (see, e.g., PubMed GeneID: 27102; see, e.g., GenBank Accession Nos. NP_055228, NP_001127807, NM_001134335, and NM_014413) is a protein kinase that phosphorylates the translation initiation factor eIF2α and regulates protein translation (Klann et al. (2004) Nat. Rev. Neurosci., 5:931-942).

The activation of the pathway controlled by eIF2αK1 has been associated with a modest increase in HbF (Hahn et al., Blood (2013) 122(4):477-85; Han et al., EMBO J. (2001) 20:6909-6919). However, in complete contrast, it is shown herein that the inhibition of eIF2αK1 raises fetal hemoglobin levels. Indeed, the genetic screen described herein for HbF inducers in human cells indicates that the loss of eIF2αK1 function increases HbF levels. Indeed, additional experiments show that the loss of eIF2αK1 increases fetal hemoglobin production in human erythroid cells, including primary cells. Without being bound by theory, the mechanism by which this occurs likely involves transcriptional and translational upregulation of fetal hemoglobin production. Thus, the role of eIF2αK1 in the suppression of fetal and, to a lesser extent, embryonic globin production has been shown herein. This role is exploited herein to treat hemoglobinopathies such as sickle cell anemia and thalassemia.

As a protein kinase, eIF2αK1 has a kinase domain that can be inhibited (e.g., by a small molecule). Additionally, eIF2αK1 can be inhibited by its natural ligand heme. This inhibition can be exploited for designing new inhibitors of eIF2αK1 (e.g., small molecule ligands that mimic heme). The kinase domain inhibitors and heme binding domain inhibitors can be used individually or in combination. Inasmuch as eIF2αK1 is expressed almost exclusively in erythroid cells, its inhibition will have little or no impact on other tissues or cells. Indeed, mice in which eIF2αK1 is deleted are fertile, appear normal, and do not present any gross abnormalities (Han et al., EMBO J. (2001) 20:6909-6919).

In accordance with the instant invention, compositions and methods are provided for increasing hemoglobin production in a cell or subject. In a particular embodiment, the method increases fetal hemoglobin and/or embryonic globin expression, particularly fetal hemoglobin. The method comprises administering at least one eIF2αK1 inhibitor to the cell, particularly an erythroid precursor cell or erythroid cell, or subject. In a particular embodiment, the subject has a hemoglobinopathy such as sickle cell disease or thalassemia. In a particular embodiment, the subject has sickle cell anemia. The eIF2αK1 inhibitor may be administered in a composition further comprising at least one pharmaceutically acceptable carrier. The methods of the instant invention may comprise administering at least two different eIF2αK1 inhibitors (e.g., two different mechanisms of action), particularly one kinase domain inhibitor and at least one heme binding domain inhibitor. In a particular embodiment, the method further comprises any means by which to induce fetal hemoglobin, such as administering at least one other fetal hemoglobin inducer. Fetal hemoglobin inducers include, without limitation, a lysine-specific demethylase 1 (LSD1) inhibitor (e.g., RN-1 (Cui et al. (2015) Blood 126(3):386-96) and tranylcypromine (TCP) (Sun et al. (2016) Reprod. Biol. Endocrinol., 14:17)), pomalidomide, hydroxyurea, and 5-azacytidine, sodium butyrate, activators of the Foxo3 pathway (e.g., metformin, phenformin, or resveratrol), histone methyltransferase (HMT) inhibitors (e.g., a histone lysine methyltransferase inhibitor, euchromatic histone-lysine N-methyltransferase 2 (EHMT2; G9a) inhibitor, euchromatic histone-lysine N-methyltransferase 1 (EHMT1; G9a-like protein (GLP)) inhibitor, UNC0638 (2-cyclohexyl-N-(1-isopropylpiperidin-4-yl)-6-methoxy-7-(3-(pyrrolidin-1-yl)propoxy) quinazolin-4-amine), chaetocin, BIX-01294, UNC 0224, UNC 0642, UNC 0631, UNC 0646, A-366 (Sweis et al. (2014) ACS Med. Chem. Lett., 5(2):205-209), etc.), and histone deacetylase (HDAC) inhibitors. In a particular embodiment, the fetal hemoglobin inducer is a histone methyltransferase (HMT) inhibitor, particularly UNC0638. In a particular embodiment, the fetal hemoglobin inducer is pomalidomide or hydroxyurea, particularly pomalidomide. The eIF2αK1 inhibitor and the fetal hemoglobin inducer can be delivered to the cell or subject sequentially or consecutively (e.g., in different compositions) and/or at the same time (e.g., in the same composition).

In accordance with another aspect of the instant invention, compositions and methods for inhibiting (e.g., reducing or slowing), treating, and/or preventing a hemoglobinopathy or thalassemia in a subject are provided. In a particular embodiment, the methods comprise administering to a subject in need thereof a therapeutically effective amount of at least one eIF2αK1 inhibitor. The eIF2αK1 inhibitor may be administered in a composition further comprising at least one pharmaceutically acceptable carrier. In a particular embodiment, the hemoglobinopathy is β-thalassemia or sickle cell anemia. In a particular embodiment, the subject has sickle cell anemia. The methods of the instant invention may comprise administering at least two different eIF2αK1 inhibitors (e.g., two different mechanisms of action), particularly one kinase domain inhibitor and at least one heme binding domain inhibitor. In a particular embodiment, the method further comprises administering at least one other fetal hemoglobin inducer to the subject. Fetal hemoglobin inducers include, without limitation, a lysine-specific demethylase 1 (LSD1) inhibitor (e.g., RN-1 (Cui et al. (2015) Blood 126(3):386-96) and tranylcypromine (TCP) (Sun et al. (2016) Reprod. Biol. Endocrinol., 14:17)), pomalidomide, hydroxyurea, and 5-azacytidine, sodium butyrate, activators of the Foxo3 pathway (e.g., metformin, phenformin, or resveratrol), histone methyltransferase (HMT) inhibitors (e.g., a histone lysine methyltransferase inhibitor, euchromatic histone-lysine N-methyltransferase 2 (EHMT2; G9a) inhibitor, euchromatic histone-lysine N-methyltransferase 1 (EHMT1; G9a-like protein (GLP)) inhibitor, UNC0638 (2-cyclohexyl-N-(1-isopropylpiperidin-4-yl)-6-methoxy-7-(3-(pyrrolidin-1-yl)propoxy) quinazolin-4-amine), chaetocin, BIX-01294, UNC 0224, UNC 0642, UNC 0631, UNC 0646, A-366 (Sweis et al. (2014) ACS Med. Chem. Lett., 5(2):205-209), etc.), and histone deacetylase (HDAC) inhibitors. In a particular embodiment, the fetal hemoglobin inducer is a histone methyltransferase (HMT) inhibitor, particularly UNC0638. In a particular embodiment, the fetal hemoglobin inducer is pomalidomide or hydroxyurea, particularly pomalidomide. The eIF2αK1 inhibitor and the fetal hemoglobin inducer can be administered to the subject sequentially or consecutively (e.g., in different compositions) and/or at the same time (e.g., in the same composition).

eIF2αK1 inhibitors are compounds which reduce eIF2αK1 activity (particularly its kinase activity) and/or the expression of eIF2αK1. In a particular embodiment, the eIF2αK1 inhibitor is specific to eIF2αK1. In a particular embodiment, the eIF2αK1 inhibitor reduces eIF2αK1 activity and/or expression to greater levels than other eukaryotic translation initiation factor 2-alpha kinases (e.g., eIF2αK2, eIF2αK3, or eIF2αK4). Examples of eIF2αK1 inhibitors include, without limitation, proteins, polypeptides, peptides, antibodies, small molecules, and nucleic acid molecules. In a particular embodiment, the eIF2αK1 inhibitor is a kinase domain inhibitor or heme binding domain inhibitor. In another embodiment, the eIF2αK1 inhibitor is an inhibitory nucleic acid molecule, such as an antisense, siRNA, or shRNA molecule (or a nucleic acid molecule encoding the inhibitory nucleic acid molecule). In a particular embodiment, the eIF2αK1 inhibitor is a CRISPR based targeting of the eIF2αK1 gene (e.g., with a guide RNA targeting the eIF2αK1 gene). In a particular embodiment, the eIF2αK1 inhibitor is a small molecule.

A variety of eIF2αK1 inhibitors are known in the art. As stated hereinabove, heme is an inhibitor of eIF2αK1 activity. Heme metabolites and heme synthesis intermediates have also been shown to inhibit eIF2αK1 activity (Miksanova et al. (2006) Biochem., 45:9894-9905). More specifically, Fe(III)-hemin, Fe(II)-heme, protoporphyrin IX, bilirubin, biliverdin, and uroporphyrin have been shown to inhibit eIF2αK1 activity (Miksanova et al. (2006) Biochem., 45:9894-9905). Quercetin has also been identified as an ATP-competitive kinase inhibitor of eIF2αK1 (Srivastava et al. (1986) Prog. Clin. Biol. Res., 213:315-8; Kanelakis et al. (2009) Adv. Hematol., 251915). A series of aminopyrazoloindanes have also been shown to be effective inhibitors of eIF2αK1 (Rosen et al. (2009) Bioorg. Med. Chem. Lett., 19(23):6548-51; incorporated herein by reference for the aminopyrazoloindane inhibitors of eIF2αK1, particularly those in Tables 2, 3, and 4). In a particular embodiment, the eIF2αK1 inhibitor is a synthetic or non-natural compound.

Clustered, regularly interspaced, short palindromic repeat (CRISPR)/Cas9 (e.g., from *Streptococcus pyogenes*) technology and gene editing are well known in the art (see, e.g., Sander et al. (2014) Nature Biotech., 32:347-355; Jinek et al. (2012) Science, 337:816-821; Cong et al. (2013) Science 339:819-823; Ran et al. (2013) Nature Protocols 8:2281-2308; Mali et al. (2013) Science 339:823-826; addgene.org/crispr/guide/). The RNA-guided CRISPR/Cas9 system involves expressing Cas9 along with a guide RNA molecule (gRNA). When coexpressed, gRNAs bind and recruit Cas9 to a specific genomic target sequence where it mediates a double strand DNA (dsDNA) break. The binding specificity of the CRISPR/Cas9 complex depends on two different elements. First, the binding complementarity between the targeted genomic DNA (genDNA) sequence and the complementary recognition sequence of the gRNA (e.g., ~18-22 nucleotides, particularly about 20 nucleotides). Second, the presence of a protospacer-adjacent motif (PAM) juxtaposed to the genDNA/gRNA complementary region (Jinek et al. (2012) Science 337:816-821; Hsu et al. (2013) Nat. Biotech., 31:827-832; Sternberg et al. (2014) Nature 507:62-67). The PAM motif for S. *Pyogenes* Cas9 has been fully characterized, and is NGG or NAG (Jinek et al. (2012) Science 337:816-821; Hsu et al. (2013) Nat. Biotech., 31: 827-832). Other PAMs of other Cas9 are also known (see, e.g., addgene.org/crispr/guide/#pam-table). Guidelines and computer-assisted methods for generating gRNAs are available (see, e.g, CRISPR Design Tool (crispr.mit.edu/); Hsu et al. (2013) Nat. Biotechnol. 31:827-832; addgene.org/CRISPR; and CRISPR gRNA Design tool—DNA2.0 (dna20.com/eCommerce/startCas9)). Typically, the PAM sequence is 3' of the DNA target sequence in the genomic sequence.

In a particular embodiment, the method comprises administering at least one Cas9 (e.g., a nucleic acid molecule encoding Cas9) and at least one gRNA (e.g., a nucleic acid molecule encoding the gRNA) to the cell or subject. In a particular embodiment, the Cas9 is *S. pyogenes* Cas9. In a particular embodiment, the targeted PAM is in the 5'UTR, promoter, or first intron. When present, a second gRNA is provided which targets anywhere from the 5'UTR to the 3'UTR of the gene, particularly within the first intron. The nucleic acids of the instant invention may be administered consecutively (before or after) and/or at the same time (concurrently). The nucleic acid molecules may be administered in the same composition or in separate compositions. In a particular embodiment, the nucleic acid molecules are delivered in a single vector (e.g., a viral vector).

In a particular embodiment, the nucleic acid molecules of the instant invention are delivered (e.g., via infection, transfection, electroporation, etc.) and expressed in cells via a vector (e.g., a plasmid), particularly a viral vector. The expression vectors of the instant invention may employ a strong promoter, a constitutive promoter, and/or a regulated promoter. In a particular embodiment, the nucleic acid molecules are expressed transiently. Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). Examples of expression vectors for expressing the molecules of the invention include, without limitation, plasmids and viral vectors (e.g., adeno-associated viruses (AAVs), adenoviruses, retroviruses, and lentiviruses).

In a particular embodiment, the guide RNA of the instant invention may comprise separate nucleic acid molecules. For example, one RNA may specifically hybridize to a target sequence (crRNA) and another RNA (trans-activating crRNA (tracrRNA)) specifically hybridizes with the crRNA. In a particular embodiment, the guide RNA is a single molecule (sgRNA) which comprises a sequence which specifically hybridizes with a target sequence (crRNA; complementary sequence) and a sequence recognized by Cas9 (e.g., a tracrRNA sequence; scaffold sequence). Examples of gRNA scaffold sequences are well known in the art (e.g., 5'-GUUUUAGAGC UAGAAAUAGC AAGUUAAAAU AAGGCUAGUC CGUUAUCAAC UUGAAAAAGU GGCACCGAGU CGGUGCUUUU; SEQ ID NO: 18). As used herein, the term "specifically hybridizes" does not mean that the nucleic acid molecule needs to be 100% complementary to the target sequence. Rather, the sequence may be at least 80%, 85%, 90%, 95%, 97%, 99%, or 100% complementary to the target sequences (e.g., the complementary between the gRNA and the genomic DNA). The greater the complementarity reduces the likelihood of undesired cleavage events at other sites of the genome. In a particular embodiment, the region of complementarity (e.g., between a guide RNA and a target sequence) is at least about 10, at least about 12, at least about 15, at least about 17, at least about 20, at least about 25, at least about 30, at least about 35, or more nucleotides. In a particular embodiment, the region of complementarity (e.g., between a guide RNA and a target sequence) is about 15 to about 25 nucleotides, about 15 to about 23 nucleotides, about 16 to about 23 nucleotides, about 17 to about 21 nucleotides, about 18 to about 22 nucleotides, or about 20 nucleotides. In a particular embodiment, the guide RNA targets a sequence or comprises a sequence (inclusive of RNA version of DNA molecules) as set forth in the Example provided herein (see, e.g., the sequences provided in Table 1 (e.g., gRNA1, gRNA2, gRNA3, gRNA4, gRNA5, or gRNA6, particularly gRNA3 or gRNA5)). In a particular embodiment, the guide RNA targets a sequence or comprises a sequence which has at least 80%, 85%, 90%, 95%, 97%, 99%, or 100% homology or identity to a sequence set forth in the Example (e.g., Table 1 provided herein; (e.g., gRNA1, gRNA2, gRNA3, gRNA4, gRNA5, or gRNA6, particularly gRNA3 or gRNA5)). The sequences may be extended or shortened by 1, 2, 3, 4, or 5 nucleotides at the end of the sequence opposite from the PAM (e.g., at the 5' end). When the sequence is extended the added nucleotides should correspond to the genomic sequence.

The above methods also encompass ex vivo methods. For example, the methods of the instant invention can comprise isolating hematopoietic cells (e.g., erythroid precursor cells) or erythroid cells from a subject, delivering at least one eIF2αK1 inhibitor to the cells, and administering the treated cells to the subject. The isolated cells may also be treated with other reagents in vitro, such as at least one fetal hemoglobin inducer, prior to administration to the subject. In a particular embodiment, the cells are not fully mature, anucleated erythrocytes.

The methods of the instant invention may further comprise monitoring the disease or disorder in the subject after administration of the composition(s) of the instant invention to monitor the efficacy of the method. For example, the subject may be monitored for characteristics of low hemoglobin or a hemoglobinopathy.

When an inhibitory nucleic acid molecule is delivered to a cell or subject, the inhibitory nucleic acid molecule may be administered directly or an expression vector may be used. In a particular embodiment, the inhibitory nucleic acid molecules are delivered (e.g., via infection, transfection, electroporation, etc.) and expressed in cells via a vector (e.g., a plasmid), particularly a viral vector. The expression vectors of the instant invention may employ a strong promoter, a constitutive promoter, and/or a regulated promoter. In a particular embodiment, the inhibitory nucleic acid molecules are expressed transiently. In a particular embodiment, the promoter is cell-type specific (e.g., erythroid cells). Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). Examples of expression vectors for expressing the molecules of the invention include, without limitation, plasmids and viral vectors (e.g., adeno-associated viruses (AAVs), adenoviruses, retroviruses, and lentiviruses).

As explained hereinabove, the compositions of the instant invention are useful for increasing hemoglobin production and for treating hemoglobinopathies and thalassemias. A therapeutically effective amount of the composition may be administered to a subject in need thereof. The dosages, methods, and times of administration are readily determinable by persons skilled in the art, given the teachings provided herein.

The components as described herein will generally be administered to a patient as a pharmaceutical preparation. The term "patient" or "subject" as used herein refers to human or animal subjects. The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The compositions of the present invention can be administered by any suitable route, for example, by injection (e.g., for local (direct) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered directly to the blood stream (e.g., intravenously). In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethyleneviny-lacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, Pa. Lippincott Williams & Wilkins. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, in which case appropriate liquid carriers, suspending agents and the like may be employed. Pharmaceutical preparations for injection are known in the art. If injection is selected as a method for administering the therapy, steps should be taken to ensure that sufficient amounts of the molecules reach their target cells to exert a biological effect.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard therapies.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient suffering from an injury, including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury, resulting in a decrease in the probability that the subject will develop conditions associated with the hemoglobinopathy or thalassemia.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated with a hemoglobinopathy or thalassemia.

As used herein, the term "subject" refers to an animal, particularly a mammal, particularly a human.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. A vector may comprise expression operons or elements such as, without limitation, transcriptional and translational control sequences, such as promoters, enhancers, translational start signals, polyadenylation signals, terminators, and the like, and which facilitate the expression of a polynucleotide or a polypeptide coding sequence in a host cell or organism.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, amino acids, or nucleic acids.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al., Current Protocols in Molecular Biology, John Wiley and Sons, Inc). Short hairpin RNA molecules (shRNA) typically consist of short complementary sequences separated by a small loop sequence wherein one of the sequences is complimentary to the gene target. shRNA molecules are typically processed into an siRNA within the cell by endonucleases. Exemplary modifications to siRNA molecules are provided in U.S. Application Publication No. 20050032733. For example, siRNA and shRNA molecules may be modified with nuclease resistant modifications (e.g., phosphorothioates, locked nucleic acids (LNA), 2'-O-methyl modifications, or morpholino linkages). Expression vectors for the expression of siRNA or shRNA molecules may employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods. Antisense oligonucleotides may be modified as described above to comprise nuclease resistant modifications.

The following example is provided to illustrate various embodiments of the present invention. It is not intended to limit the invention in any way.

Example

A CRISPR screening strategy (Shi et al. (2015) Nat. Biotechnol., 33(6):661-7) was employed to identify regulators of fetal globin expression. Clustered, regularly interspaced, short palindromic repeat (CRISPR)/Cas9 technology is well known in the art (see, e.g., Sander et al. (2014) Nature Biotech., 32:347-355; Jinek et al. (2012) Science, 337:816-821; Cong et al. (2013) Science 339:819-823; Ran et al. (2013) Nature Protocols 8:2281-2308; Mali et al. (2013) Science 339:823-826). Cas9 possesses two nuclease domains, a RuvC-like nuclease domain and a HNH-like nuclease domain, and is responsible for the destruction of the target DNA (Jinek et al. (2012) Science, 337:816-821; Sapranauskas et al. (2011) Nucleic Acids Res. 39:9275-9282). The two nucleases generate double-stranded breaks. The double-stranded endonuclease activity of Cas9 requires a target sequence (e.g., ~20 nucleotides, see above) and a short conserved sequence (~2-5 nucleotides; e.g., 3 nucleotides) known as protospacer-associated motif (PAM), which follows immediately 3'—of the CRISPR RNA (crRNA) complementary sequence (Jinek et al. (2012) Science, 337: 816-821; Nishimasu et al. (2014) Cell 156(5):935-49; Swarts et al. (2012) PLoS One, 7:e35888; Sternberg et al. (2014) Nature 507(7490):62-7). The double strand break can be repaired by non-homologous end joining (NHEJ) pathway yielding an insertion and/or deletion or, in the presence of a donor template, by homology-directed repair (HDR) pathway for replacement mutations (Overballe-Petersen et al. (2013) Proc. Natl. Acad. Sci. U.S.A. 110:19860-19865; Gong et al. (2005) Nat. Struct. Mol. Biol. 12:304-312). The RNA-guided CRISPR/Cas9 system involves expressing Cas9 along with a guide RNA molecule (gRNA). When coexpressed, gRNAs bind and recruit Cas9 to a specific genomic target sequence where it mediates a double strand DNA (dsDNA) break and activates the dsDNA break repair machinery. Specific DNA fragments can be deleted when two gRNA/Cas9 complexes generate dsDNA breaks at relative proximity, and the genomic DNA is repaired by non-homologous end joining.

Briefly, cells from a human umbilical cord blood-derived erythroid cells progenitor cell line (HUDEP2) expressing Cas9 were transduced with a lentiviral library of guideRNAs (gRNAs). The library targeted over 500 different kinase domains with 6 guides per domain (i.e., over 3000 independent guides). Cells were then stained with fetal hemoglobin antibody and positive cells were sorted. The results showed that all 6 guides for eIF2αK1 resulted in enriched fetal globin expression.

These results were confirmed in HUDEP-2 cells by individually expressing each one of the six gRNAs targeting eIF2αK1, a gRNA targeting BCL11A exon 2 (positive control; BCL11A is a repressor of HbF expression), one of two gRNAs targeting death associated protein kinase 2 (DAPK2), one of two gRNAs targeting transforming growth factor beta receptor 2 (TGFBR2), or a negative control gRNA. Table 1 provides sequences of the gRNAs fluorescence-activated cell sorting (FACS) with an HbF antibody shows that the eIF2αK1 gRNAs significantly increased expression of HbF compared to the other gRNAs and negative controls (FIG. 1A). A quantitative reverse transcription PCR (RT-qPCR) analysis was also performed on the above cells to measure mRNA levels. As seen in FIG. 1B, the eIF2αK1 gRNAs significantly increased gamma globin RNA levels compared to the other gRNAs and negative controls. FIG. 1C provides a representative FACS analysis for sgRNA #5 showing increased HbF production. FIG. 1D provides a graph of HbF flow cytometry of cells expressing indicated sgRNAs over two experiments. Western blot analysis confirmed the decreased expression of eIF2αK1 (HRI) and increased expression of γ-globin with sgRNA #3 and sgRNA #5.

TABLE 1 gRNA sequences.

| CRISPR sgRNA name | Target Sequence | SEQ ID NO |
|---|---|---|
| BCL11A Exon2 sgRNA | TGAACCAGACCACGGCCCGT | 1 |
| eIF2αK1 sgRNA1 | TCTGGAAGTGCTCTCCGACC | 2 |
| eIF2αK1 sgRNA2 | GTATCCACCTTTTCCTAAGA | 3 |
| eIF2αK1 sgRNA3 | TTTTAGTTGCACCCTTAATC | 4 |
| eIF2αK1 sgRNA4 | TTGTTGGCTATCACACCGCG | 5 |
| eIF2αK1 sgRNA5 | ATAGTCGAGAGAAACAAGCG | 6 |
| eIF2αK1 sgRNA6 | TGGTGAACTTGAGTCGACCC | 7 |
| Neg02 sgRNA | GACCGGAACGATCTCGCGTA | 8 |

In addition to the above, a whole proteome mass spectrometry analysis of cells transduced with a gRNA targeting eIF2αK1 was performed. As seen in FIG. 2, fetal globin expression increased more than two fold upon transduction with eIF2αK1 gRNA #3 or gRNA #5.

Combination experiments with the immunomodulatory pomalidomide, which is an HbF inducer, were also performed. If eIF2αK1 inhibition works at least in part by altering protein translation, additive effects may be observed when using compounds that predominantly affect transcription of fetal globin genes. Briefly, HUDEP-2 expressing Cas9 cells were transduced with eIF2αK1 gRNA #3, eIF2αK1 gRNA #5, a gRNA targeting BCL11A exon 2, or a negative control gRNA. The cells were then incubated with or without pomalidomide. As seen in FIG. 3, the combination of eIF2αK1 inhibition and pomalidomide greatly increased the number of HbF positive cells. Indeed, the results with pomalidomide in combination with eIF2αK1 inhibition were very strong in three independent experiments, even stronger than those observed with Bcl11A inhibition and pomalidomide. This demonstrates that a compound that inhibits eIF2αK1 can be combined with pomalidomide or other HbF inducers to achieve a greater therapeutic index.

In additional experiments, eIF2αK1 was knocked down in primary human erythroid cells using shRNAs, as editing was not efficient enough in primary cells. Fetal hemoglobin was found to be upregulated in a manner comparable to or exceeding that of Bcl11A depletion (positive control). As seen in FIG. 4, two of the four shRNA (#1 and #4) dramatically increased HbF production in human primary cells. Table 2 provides the sequences of the shRNA molecules.

TABLE 2 shRNA sequences.

| shRNA name | Target Sequence | SEQ ID NO |
| --- | --- | --- |
| ZBTB7A shRNA2 | AAGTCGATCTCGTACACGTTC | 9 |
| ZBTB7A shRNA4 | AATAGGTTTGTGTCTCAGTGG | 10 |
| BCL11A shRNA1 | AATCCATGAGTGTTCTGTGCG | 11 |
| BCL11A shRNA2 | TAAACAATCGTCATCCTCTGG | 12 |

TABLE 2-continued shRNA sequences.

| shRNA name | Target Sequence | SEQ ID NO |
| --- | --- | --- |
| eIF2αK1 shRNA1 | TTAACACCACATTGCTCTCTG | 13 |
| eIF2αK1 shRNA2 | ATTAAGTGAGTAATAGCTCTG | 14 |
| eIF2αK1 shRNA3 | TAAACGTCTGGCAAAGTAGC | 15 |
| eIF2αK1 shRNA4 | TAAACCTGTTAGAACTTCTGC | 16 |
| SC shRNA | AAATTATTAGCGCTATCGCGC | 17 |

FIG. 5A provides a representative HbF flow cytometry on day 14 of CD34+ erythroid differentiation. LRF shRNA and shRNA 1 and 2 increased HbF expression. Leukemia/lymphoma-related factor (LRF), as with BCL11A, represses expression of fetal hemoglobin (Masuda et al. (2016) Science 351(6270): 285-289). FIG. 5B provides a summary of HbF flow cytometry experiments. FIG. 5C provides γ-globin mRNA as fraction of γ-globin+β-globin by RT-qPCR on day 12. FIG. 5D provides RNA-seq for CD34+ cells on day 12. FIG. 5E shows an HPLC analysis of samples from cell expressing annotated shRNAs, at day 14 of differentiation. FIG. 5F provides images of sickle cell patient-derived erythroid cultures showing that eIF2αK1 shRNA1 and eIF2αK1 shRN2 decreased the number of sickle cells.

Further experiments demonstrate that HRI regulates BCL11A protein levels. Western blot analyses were performed with indicated antibodies (FIG. 6A) in cells uninfected, or infected with virus expressing scrambled or HRI shRNAs on day 14 of differentiation. BCL11A expression is decreased with HRI shRNAs. FIG. 6A also shows BCL11A mRNA levels in HRI knock down cells as fraction of SC shRNA expressing cells. FIG. 6B shows BCL11A cDNA rescue in HRI depleted HUDEP2 clonal cell lines.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of increasing the level of fetal hemoglobin in a cell or subject, the method comprising administering at least one eukaryotic translation initiation factor 2-alpha kinase 1 (eIF2αK1) inhibitor to the cell or subject, wherein the subject has sickle cell anemia.

2. The method of claim 1, wherein the eIF2αK1 inhibitor is a small molecule.

3. The method of claim 1, wherein the eIF2αK1 inhibitor is a kinase domain inhibitor or a heme binding domain inhibitor.

4. The method of claim 1, wherein the cell is an erythroid cell.

5. The method of claim 1, further comprising administering at least one fetal hemoglobin inducer to the cell or subject.

6. The method of claim 5, wherein said fetal hemoglobin inducer is pomalidomide.

7. The method of claim 5, wherein said fetal hemoglobin inducer is a histone methyltransferase (HMT) inhibitor.

8. The method of claim 7, wherein said HMT inhibitor is UNC0638.

9. A method of treating a hemoglobinopathy in a subject in need thereof, the method comprising administering a composition comprising at least one eukaryotic translation initiation factor 2-alpha kinase 1 (eIF2αK1) inhibitor and a pharmaceutically acceptable carrier to the subject, wherein the subject has sickle cell anemia.

10. The method of claim 9, wherein the eIF2αK1 inhibitor is a small molecule.

11. The method of claim 9, wherein the eIF2αK1 inhibitor is a kinase domain inhibitor or a heme binding domain inhibitor.

12. The method of claim 9, further comprising administering at least one fetal hemoglobin inducer to the subject.

13. The method of claim 12, wherein said fetal hemoglobin inducer is pomalidomide.

14. The method of claim 12, wherein said fetal hemoglobin inducer is a histone methyltransferase (HMT) inhibitor.

15. The method of claim 14, wherein said HMT inhibitor is UNC0638.

16. The method of claim 9, wherein the eIF2αK1 inhibitor is contained within a cell administered to the subject.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Target Sequence

<400> SEQUENCE: 1
tgaaccagac cacggcccgt                                              20

<210> SEQ ID NO 2
<211> LENGTH: 20
<212> TYPE: DNA
<213> ORGANISM: Artificial Sequence
<220> FEATURE:
<223> OTHER INFORMATION: Target Sequence

<400> SEQUENCE: 2
tctggaagtg ctctccgacc                                              20
```

```
<210> SEQ ID NO 3
<211> LENGTH: 20
<212> TYPE: DNA
<213> ORGANISM: Artificial Sequence
<220> FEATURE:
<223> OTHER INFORMATION: Target Sequence

<400> SEQUENCE: 3
gtatccacct tttcctaaga                                               20

<210> SEQ ID NO 4
<211> LENGTH: 20
<212> TYPE: DNA
<213> ORGANISM: Artificial Sequence
<220> FEATURE:
<223> OTHER INFORMATION: Target Sequence

<400> SEQUENCE: 4
ttttagttgc acccttaatc                                               20

<210> SEQ ID NO 5
<211> LENGTH: 20
<212> TYPE: DNA
<213> ORGANISM: Artificial Sequence
<220> FEATURE:
<223> OTHER INFORMATION: Target Sequence

<400> SEQUENCE: 5
ttgttggcta tcacaccgcg                                               20

<210> SEQ ID NO 6
<211> LENGTH: 20
<212> TYPE: DNA
<213> ORGANISM: Artificial Sequence
<220> FEATURE:
<223> OTHER INFORMATION: Target Sequence

<400> SEQUENCE: 6
atagtcgaga gaaacaagcg                                               20

<210> SEQ ID NO 7
<211> LENGTH: 20
<212> TYPE: DNA
<213> ORGANISM: Artificial Sequence
<220> FEATURE:
<223> OTHER INFORMATION: Target Sequence

<400> SEQUENCE: 7
tggtgaactt gagtcgaccc                                               20

<210> SEQ ID NO 8
<211> LENGTH: 20
<212> TYPE: DNA
<213> ORGANISM: Artificial Sequence
<220> FEATURE:
<223> OTHER INFORMATION: Target Sequence

<400> SEQUENCE: 8
gaccggaacg atctcgcgta                                               20

<210> SEQ ID NO 9
<211> LENGTH: 21
<212> TYPE: DNA
<213> ORGANISM: Artificial Sequence
<220> FEATURE:
<223> OTHER INFORMATION: Target Sequence
```

```
<400> SEQUENCE: 9
aagtcgatct cgtacacgtt c                                              21

<210> SEQ ID NO 10
<211> LENGTH: 21
<212> TYPE: DNA
<213> ORGANISM: Artificial Sequence
<220> FEATURE:
<223> OTHER INFORMATION: Target Sequence

<400> SEQUENCE: 10
aataggtttg tgtctcagtg g                                              21

<210> SEQ ID NO 11
<211> LENGTH: 21
<212> TYPE: DNA
<213> ORGANISM: Artificial Sequence
<220> FEATURE:
<223> OTHER INFORMATION: Target Sequence

<400> SEQUENCE: 11
aatccatgag tgttctgtgc g                                              21

<210> SEQ ID NO 12
<211> LENGTH: 21
<212> TYPE: DNA
<213> ORGANISM: Artificial Sequence
<220> FEATURE:
<223> OTHER INFORMATION: Target Sequence

<400> SEQUENCE: 12
taaacaatcg tcatcctctg g                                              21

<210> SEQ ID NO 13
<211> LENGTH: 21
<212> TYPE: DNA
<213> ORGANISM: Artificial Sequence
<220> FEATURE:
<223> OTHER INFORMATION: Target Sequence

<400> SEQUENCE: 13
ttaacaccac attgctctct g                                              21

<210> SEQ ID NO 14
<211> LENGTH: 21
<212> TYPE: DNA
<213> ORGANISM: Artificial Sequence
<220> FEATURE:
<223> OTHER INFORMATION: Target Sequence

<400> SEQUENCE: 14
attaagtgag taatagctct g                                              21

<210> SEQ ID NO 15
<211> LENGTH: 20
<212> TYPE: DNA
<213> ORGANISM: Artificial Sequence
<220> FEATURE:
<223> OTHER INFORMATION: Target Sequence

<400> SEQUENCE: 15
taaacgtctg gcaaagtagc                                                20

<210> SEQ ID NO 16
```

```
<211> LENGTH: 21
<212> TYPE: DNA
<213> ORGANISM: Artificial Sequence
<220> FEATURE:
<223> OTHER INFORMATION: Target Sequence

<400> SEQUENCE: 16
taaacctgtt agaacttctg c                                              21

<210> SEQ ID NO 17
<211> LENGTH: 21
<212> TYPE: DNA
<213> ORGANISM: Artificial Sequence
<220> FEATURE:
<223> OTHER INFORMATION: Target Sequence

<400> SEQUENCE: 17
aaattattag cgctatcgcg c                                              21

<210> SEQ ID NO 18
<211> LENGTH: 80
<212> TYPE: RNA
<213> ORGANISM: Artificial Sequence
<220> FEATURE:
<223> OTHER INFORMATION: Scaffold Sequence

<400> SEQUENCE: 18
guuuuagagc uagaaauagc aaguuaaaau aaggcuaguc cguuaucaac uugaaaaagu    60
ggcaccgagu cggugcuuuu                                                80

<210> SEQ ID NO 19
<211> LENGTH: 630
<212> TYPE: PRT
<213> ORGANISM: Homo Sapiens

<400> SEQUENCE: 19

Met Gln Gly Gly Asn Ser Gly Val Arg Lys Arg Glu Glu Glu Gly Asp
1               5                   10                  15

Gly Ala Gly Ala Val Ala Ala Pro Pro Ala Ile Asp Phe Pro Ala Glu
            20                  25                  30

Gly Pro Asp Pro Glu Tyr Asp Glu Ser Asp Val Pro Ala Glu Ile Gln
        35                  40                  45

Val Leu Lys Glu Pro Leu Gln Gln Pro Thr Phe Pro Phe Ala Val Ala
    50                  55                  60

Asn Gln Leu Leu Leu Val Ser Leu Leu Glu His Leu Ser His Val His
65                  70                  75                  80

Glu Pro Asn Pro Leu Arg Ser Arg Gln Val Phe Lys Leu Leu Cys Gln
                85                  90                  95

Thr Phe Ile Lys Met Gly Leu Leu Ser Ser Phe Thr Cys Ser Asp Glu
            100                 105                 110

Phe Ser Ser Leu Arg Leu His His Asn Arg Ala Ile Thr His Leu Met
        115                 120                 125

Arg Ser Ala Lys Glu Arg Val Arg Gln Asp Pro Cys Glu Asp Ile Ser
    130                 135                 140

Arg Ile Gln Lys Ile Arg Ser Arg Glu Val Ala Leu Glu Ala Gln Thr
145                 150                 155                 160

Ser Arg Tyr Leu Asn Glu Phe Glu Leu Ala Ile Leu Gly Lys Gly Gly
                165                 170                 175

Gly Tyr Gly Arg Val Tyr Lys Val Arg Asn Lys Leu Asp Gly Gln Tyr
            180                 185                 190
```

```
Tyr Ala Ile Lys Lys Ile Leu Ile Lys Gly Ala Thr Lys Thr Val Cys
            195                 200                 205
Met Lys Val Leu Arg Glu Val Lys Val Leu Ala Gly Leu Gln His Pro
210                 215                 220
Asn Ile Val Gly Tyr His Thr Ala Trp Ile Glu His Val His Val Ile
225                 230                 235                 240
Gln Pro Arg Ala Asp Arg Ala Ala Ile Glu Leu Pro Ser Leu Glu Val
                245                 250                 255
Leu Ser Asp Gln Glu Glu Asp Arg Glu Gln Cys Gly Val Lys Asn Asp
            260                 265                 270
Glu Ser Ser Ser Ser Ile Ile Phe Ala Glu Pro Thr Pro Glu Lys
            275                 280                 285
Glu Lys Arg Phe Gly Glu Ser Asp Thr Glu Asn Gln Asn Asn Lys Ser
            290                 295                 300
Val Lys Tyr Thr Thr Asn Leu Val Ile Arg Glu Ser Gly Glu Leu Glu
305                 310                 315                 320
Ser Thr Leu Glu Leu Gln Glu Asn Gly Leu Ala Gly Leu Ser Ala Ser
                325                 330                 335
Ser Ile Val Glu Gln Gln Leu Pro Leu Arg Arg Asn Ser His Leu Glu
            340                 345                 350
Glu Ser Phe Thr Ser Thr Glu Glu Ser Ser Glu Glu Asn Val Asn Phe
            355                 360                 365
Leu Gly Gln Thr Glu Ala Gln Tyr His Leu Met Leu His Ile Gln Met
            370                 375                 380
Gln Leu Cys Glu Leu Ser Leu Trp Asp Trp Ile Val Glu Arg Asn Lys
385                 390                 395                 400
Arg Gly Arg Glu Tyr Val Asp Glu Ser Ala Cys Pro Tyr Val Met Ala
                405                 410                 415
Asn Val Ala Thr Lys Ile Phe Gln Glu Leu Val Glu Gly Val Phe Tyr
                420                 425                 430
Ile His Asn Met Gly Ile Val His Arg Asp Leu Lys Pro Arg Asn Ile
            435                 440                 445
Phe Leu His Gly Pro Asp Gln Gln Val Lys Ile Gly Asp Phe Gly Leu
            450                 455                 460
Ala Cys Thr Asp Ile Leu Gln Lys Asn Thr Asp Trp Thr Asn Arg Asn
465                 470                 475                 480
Gly Lys Arg Thr Pro Thr His Thr Ser Arg Val Gly Thr Cys Leu Tyr
                485                 490                 495
Ala Ser Pro Glu Gln Leu Glu Gly Ser Glu Tyr Asp Ala Lys Ser Asp
                500                 505                 510
Met Tyr Ser Leu Gly Val Val Leu Leu Glu Leu Phe Gln Pro Phe Gly
            515                 520                 525
Thr Glu Met Glu Arg Ala Glu Val Leu Thr Gly Leu Arg Thr Gly Gln
            530                 535                 540
Leu Pro Glu Ser Leu Arg Lys Arg Cys Pro Val Gln Ala Lys Tyr Ile
545                 550                 555                 560
Gln His Leu Thr Arg Arg Asn Ser Ser Gln Arg Pro Ser Ala Ile Gln
                565                 570                 575
Leu Leu Gln Ser Glu Leu Phe Gln Asn Ser Gly Asn Val Asn Leu Thr
            580                 585                 590
Leu Gln Met Lys Ile Ile Glu Gln Glu Lys Glu Ile Ala Glu Leu Lys
            595                 600                 605
```

Lys Gln Leu Asn Leu Leu Ser Gln Asp Lys Gly Val Arg Asp Asp Gly
    610                 615                 620

Lys Asp Gly Gly Val Gly
625                 630

<210> SEQ ID NO 20
<211> LENGTH: 4465
<212> TYPE: DNA
<213> ORGANISM: Homo Sapiens

<400> SEQUENCE: 20

| | | | | | | |
|---|---|---|---|---|---|---|
| ccccagtgaa | ggtgcgcgcg | tggcggaggc | tggttttccg | tctggtgagg | ggttacttcc | 60 |
| gggtcggacg | gcgctagctg | cagcatcgga | gtgtggcagt | gctgggctgg | ccggcgggct | 120 |
| gggctgcggc | ccgcgcgcgg | ccggcgatgc | agggggggcaa | ctccgggtgtc | cgcaagcgcg | 180 |
| aagaggaggg | cgacggggct | ggggctgtgg | ctgcgccgcc | ggccatcgac | tttcccgccg | 240 |
| agggcccgga | ccccgaatat | gacgaatctg | atgttccagc | agaaatccag | gtgttaaaag | 300 |
| aaccccctaca | acagccaacc | ttcccttttg | cagttgcaaa | ccaactcttg | ctggtttctt | 360 |
| tgctggagca | cttgagccac | gtgcatgaac | caaacccact | tcgttcaaga | caggtgttta | 420 |
| agctactttg | ccagacgttt | atcaaaatgg | ggctgctgtc | ttctttcact | tgtagtgacg | 480 |
| agtttagctc | attgagacta | catcacaaca | gagctattac | tcacttaatg | aggtctgcta | 540 |
| aagagagagt | tcgtcaggat | ccttgtgagg | atatttctcg | tatccagaaa | atcagatcaa | 600 |
| gggaagtagc | cttggaagca | caaacttcac | gttacttaaa | tgaatttgaa | gaacttgcca | 660 |
| tcttaggaaa | aggtggatac | ggaagagtat | acaaggtcag | gaataaatta | gatggtcagt | 720 |
| attatgcaat | aaaaaaaatc | ctgattaagg | gtgcaactaa | aacagtttgc | atgaaggtcc | 780 |
| tacgggaagt | gaaggtgctg | gcaggtcttc | agcaccccaa | tattgttggc | tatcacaccg | 840 |
| cgtggataga | acatgttcat | gtgattcagc | cacgagcaga | cagagctgcc | attgagttgc | 900 |
| catctctgga | agtgctctcc | gaccaggaag | aggacagaga | gcaatgtggt | gttaaaaatg | 960 |
| atgaaagtag | cagctcatcc | attatctttg | ctgagcccac | cccagaaaaa | gaaaaacgct | 1020 |
| ttggagaatc | tgacactgaa | aatcagaata | acaagtcggt | gaagtacacc | accaatttag | 1080 |
| tcataagaga | atctggtgaa | cttgagtcga | ccctggagct | ccaggaaaat | ggcttggctg | 1140 |
| gtttgtctgc | cagttcaatt | gtggaacagc | agctgccact | caggcgtaat | tcccacctag | 1200 |
| aggagagttt | cacatccacc | gaagaatctt | ccgaagaaaa | tgtcaacttt | ttgggtcaga | 1260 |
| cagaggcaca | gtaccacctg | atgctgcaca | tccagatgca | gctgtgtgag | ctctcgctgt | 1320 |
| gggattggat | agtcgagaga | aacaagcggg | gccgggagta | tgtggacgag | tctgcctgtc | 1380 |
| cttatgttat | ggccaatgtt | gcaacaaaaa | ttttttcaaga | attggtagaa | ggtgtgtttt | 1440 |
| acatacataa | catgggaatt | gtgcaccgag | atctgaagcc | aagaaatatt | tttcttcatg | 1500 |
| gccctgatca | gcaagtaaaa | ataggagact | ttggtctggc | ctgcacagac | atcctacaga | 1560 |
| agaacacaga | ctggaccaac | agaaacggga | agagaacacc | aacacatacg | tccagagtgg | 1620 |
| gtacttgtct | gtacgcttca | cccgaacagt | tggaaggatc | tgagtatgat | gccaagtcag | 1680 |
| atatgtacag | cttgggtgtg | gtcctgctag | agctcttttca | gccgtttgga | acagaaatgg | 1740 |
| agcgagcaga | agttctaaca | ggtttaagaa | ctggtcagtt | gccggaatcc | ctccgtaaaa | 1800 |
| ggtgtccagt | gcaagccaag | tatatccagc | acttaacgag | aaggaactca | tcgcagagac | 1860 |
| catctgccat | tcagctgctg | cagagtgaac | ttttccaaaa | ttctggaaat | gttaacctca | 1920 |
| ccctacagat | gaagataata | gagcaagaaa | aagaaattgc | agaactaaag | aagcagctaa | 1980 |

```
acctcctttc tcaagacaaa ggggtgaggg atgacggaaa ggatgggggc gtgggatgaa    2040
agtggactta acttttaagg tagttaactg gaatgtaaat ttttaatctt tattagggta    2100
tagttggtac aatgcttcgt tgtatttagt aagcctttac aagacttgtt aaagatgtca    2160
gagtgcccca agctgccgtt ccttcccttc ctgcccaca agctccttt cctgaatttc     2220 ctacctaaat attaaccata tgcctagtct ctgaaactaa aaacttggac ctcatcctca    2280
attattttct cctttcaact ctgttgaccc tctgtctggt cttcctctag aaggtaccgc    2340
agaaattgat gtgtgctccc tgccctcgtc actgcccaag cccgggcctg cacatactca    2400
ctggactgtt ccagttttga cagctgccag tcttcctgcc cctttcacac tgcagctgaa    2460
gttcattacc tgaaggacgc ctcatcattt cattccttgg ctccaaacct tctgctgcct    2520
ctaagataaa agctcaactt cttaacagtg tacagtgtgc aacttccaac ctttttatct    2580
gttctctcca ccttcagttt agcgtcattc caaaaccaca cccttgcaaa gctttgtact    2640
ccgcacccca gatgatctcc aggcagctca gatctctttc ctgcctttgc cctgcactgt    2700
tccccggtac ttcctccttt attgtagcac tcagctcccc agccaatctg tacatccctc    2760
agaggcagcg atctgatgaa ttggttttg aatcccagaa agggtctgcc atggagttgg     2820
cagtcatcac ggtagatggc gtatgatttt gctgaatttt aaataaaatg aaaaccataa    2880
attacatgat gcttttattg acacttgaca actggcctaa ataaaaagac tctgactcta    2940
atacaagtcc ccttactgat aataggcatg aaagagcacc attcttaaaa tctaaaccct    3000
ttaaaatcag ttacggcaat tcacttaagg agcttgaggg ccgtgttaaa aggagccagg    3060
ttttcacaag acctcatcca cctctgcaca ttggctggca ctgtcacact gcagcctccg    3120
atctgctgga gtacagacca cagcaccacg tctgctacgg tgagttcatt cccagcgagc    3180
caagggctct tcccaagagc agagttcatg gagcggaaaa cagcggcttt ttctttactg    3240
cttccctctt ttaactgaaa aatcgcaata tctacccagc tatctataag ggttgcgttg    3300
acagcattat gcttctggcc aaacagagag aacaagaaac gtgcaatgtt cccttcgcct    3360
tcgatggggc acatcgtctg gatgctgaat ttcatctgcg tcttcggcac tgaaaagaaa    3420
aaacacgcca ggtagcatca ccagagcagc cctgagggaa gtactcgcac agtggggaag    3480
gggacagtca ccaaacacca cagactgatg acatgggaaa gggtgttttc aagaagaaca    3540 tcacatttc agtctgtctc taagatgctt actactgaaa agggtttaag tgcaaactat     3600
gttaaaaaag taaccaaaga gtcattcctg gtatttgatt atgacacttc tgaagctaga    3660
agggacctca gaccacctgc tccaatccct gctgcctaag gttttgggg ctgagggctg     3720 gaaacccagg agctgcatct cccaggctct tggcctcata atcgccttct gtgagactga    3780
gggcaattaa gatatgaatg acatgaactc gcttatctcc atatcaacat aaaccagaag    3840
aggcatacat ctgtgggata gtcaatacat aacatcctat ctttatatgg ccatatgaga    3900
agataacttc agtgtcccta tgatggtaag ttcttgaatg tgagggcaag atggctgtga    3960
tagccatgac tccccgcttt gctggttgg acagaacccc cttccccaaa tgctcacagt      4020
cccccccttg agctgtgtct cactcagaga ccctaaattt tgcagacgaa caagggcatc    4080
tttgcgttgc ttcatctctg ctcctcctct agaactatcc cacaggcttt ctagacttag    4140
aatatctgac ctgatgcaaa tcgctatgtg gccagtatgc cacagaatgt cctaaaccct    4200
tgctgcctct tatcaaaacc atgttgcaca tctcatcata tagtacagct aacccttgaa    4260
cagtgggggg gttagggaca ctgaccccg actgctgtgc agtcgaaaat ccacataaaa      4320
```

```
cttctgactc cttcaaaact taagcactaa tagcctacta ttcatgggaa gccttaccca    4380
tcacagttga ttaacacgtt ttgtatggtc tgtatattat atgctatatt cttacaataa    4440
acttgagaaa atgttaagaa aataa                                          4465
```